US011191428B1

(12) United States Patent
Chang et al.

(10) Patent No.: US 11,191,428 B1
(45) Date of Patent: Dec. 7, 2021

(54) MEDICAL/DENTAL HANDPIECE

(71) Applicant: SyACT LLP, Plantation, FL (US)

(72) Inventors: Jeffrey Wen Wei Chang, Hong Kong (HK); George Bruder, West Palm Beach, FL (US); Sergio Kuttler, Plantation, FL (US); Anil Kishen, Mississauga (CA)

(73) Assignee: SYACT, LLP, Plantation, FL (US)

( * ) Notice: Subject to any disclaimer, the term of this patent is extended or adjusted under 35 U.S.C. 154(b) by 0 days.

(21) Appl. No.: 16/931,247

(22) Filed: Jul. 16, 2020

(51) Int. Cl.
| *A61B 1/24* | (2006.01) |
| *A61B 1/06* | (2006.01) |
| *A61B 1/00* | (2006.01) |
| *A61C 1/08* | (2006.01) |
| *A61C 5/40* | (2017.01) |

(52) U.S. Cl.
CPC ............ *A61B 1/24* (2013.01); *A61B 1/00135* (2013.01); *A61B 1/06* (2013.01); *A61C 1/088* (2013.01); *A61C 5/40* (2017.02)

(58) Field of Classification Search
CPC .... A61C 5/40; A61C 5/42; A61C 5/46; A61C 5/50; A61C 5/55; A61C 1/00; A61C 1/088; A61C 1/0046; A61B 1/24; A61B 1/0623
See application file for complete search history.

(56) References Cited

U.S. PATENT DOCUMENTS

| 5,409,376 | A | * | 4/1995 | Murphy | ................ | A61B 18/22 |
| | | | | | | 433/29 |
| 5,897,321 | A | * | 4/1999 | Goodman | ............ | A61C 1/0046 |
| | | | | | | 433/215 |
| 6,360,395 | B2 | * | 3/2002 | Blaustein | ................ | A61C 17/22 |
| | | | | | | 15/22.1 |
| 7,261,561 | B2 | | 8/2007 | Ruddle et al. | | |
| 9,017,073 | B2 | * | 4/2015 | Madry | ................. | A61C 17/005 |
| | | | | | | 433/125 |
| 9,987,200 | B2 | | 6/2018 | Kishen | | |
| 2005/0050659 | A1 | * | 3/2005 | Chan | ...................... | A61C 17/22 |
| | | | | | | 15/22.1 |
| 2007/0264608 | A1 | * | 11/2007 | Brosnihan | ............ | A61N 5/0624 |
| | | | | | | 433/29 |
| 2010/0330523 | A1 | * | 12/2010 | Kert | ....................... | A61N 5/062 |
| | | | | | | 433/29 |
| 2013/0086758 | A1 | * | 4/2013 | Boutoussov | ......... | A61C 17/349 |
| | | | | | | 15/22.1 |
| 2019/0290397 | A1 | | 9/2019 | Bruder, III et al. | | |

FOREIGN PATENT DOCUMENTS

WO WO2018009864 A1 * 1/2018

* cited by examiner

*Primary Examiner* — Edward Moran
(74) *Attorney, Agent, or Firm* — Sandberg Phoenix & von Gontard, P.C.

(57) ABSTRACT

A medical/dental handpiece comprises a housing having distal portion, the head portion having a bottom surface defining an opening. A motor and a light source are positioned with the handpiece, and the handpiece removably receives a light guide in alignment with the light source, to receive light from the light source. The light guide includes a probe which can be positioned adjacent or within a treatment area. The handpiece can be operated to activate only the light source, such that light is directed through the probe to or into the treatment area, to activate only the motor to rotationally or reciprocatingly drive the light guide, or to activate both the light source and the motor.

32 Claims, 25 Drawing Sheets

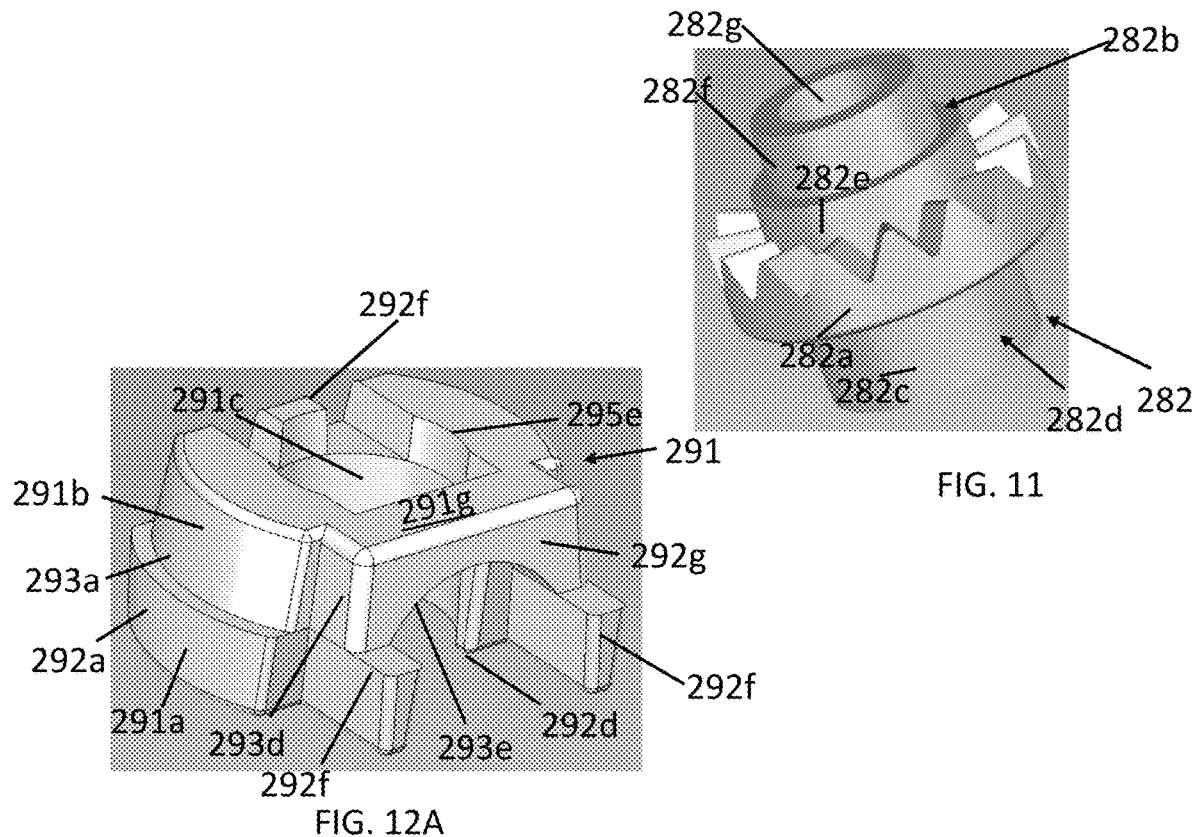
FIG. 11
FIG. 12A
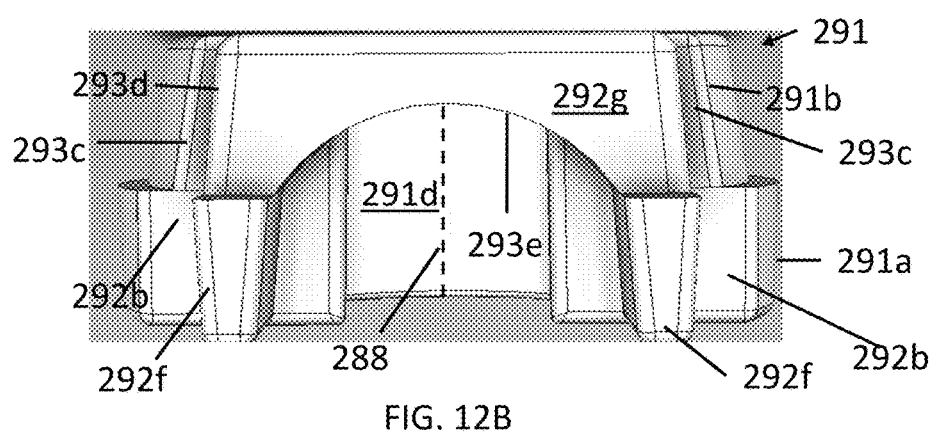
FIG. 12B

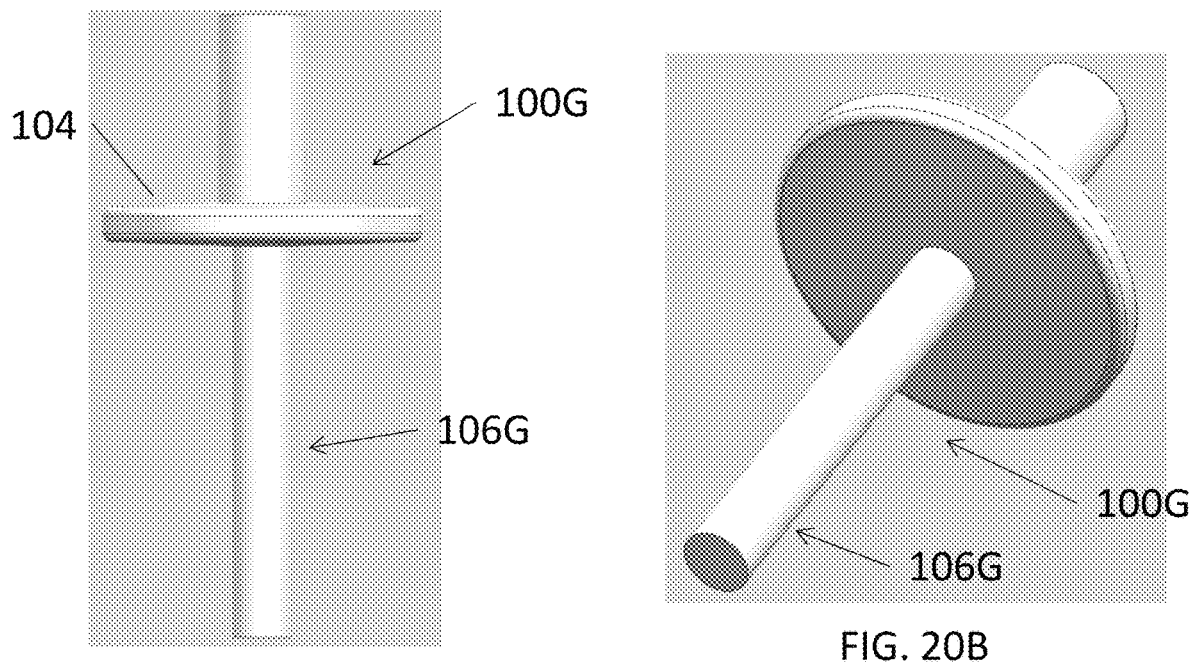
FIG. 20A
FIG. 20B
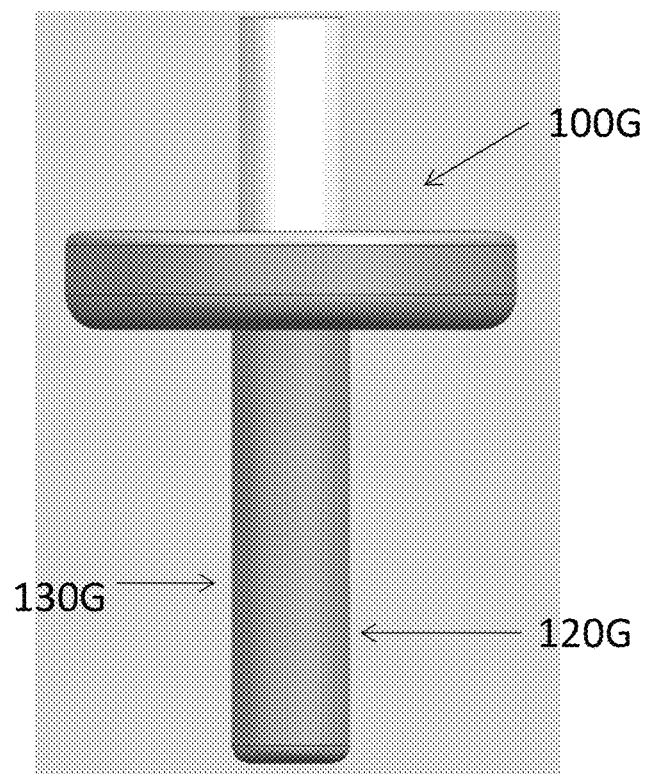
FIG. 20C

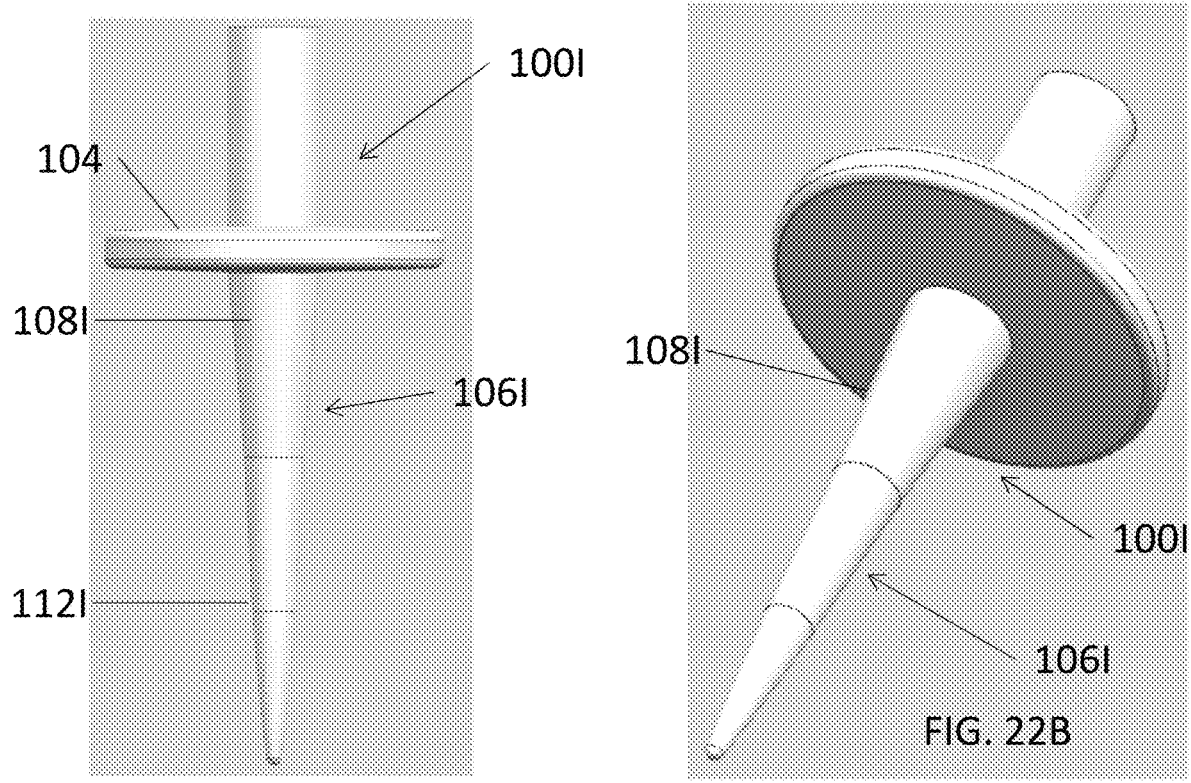
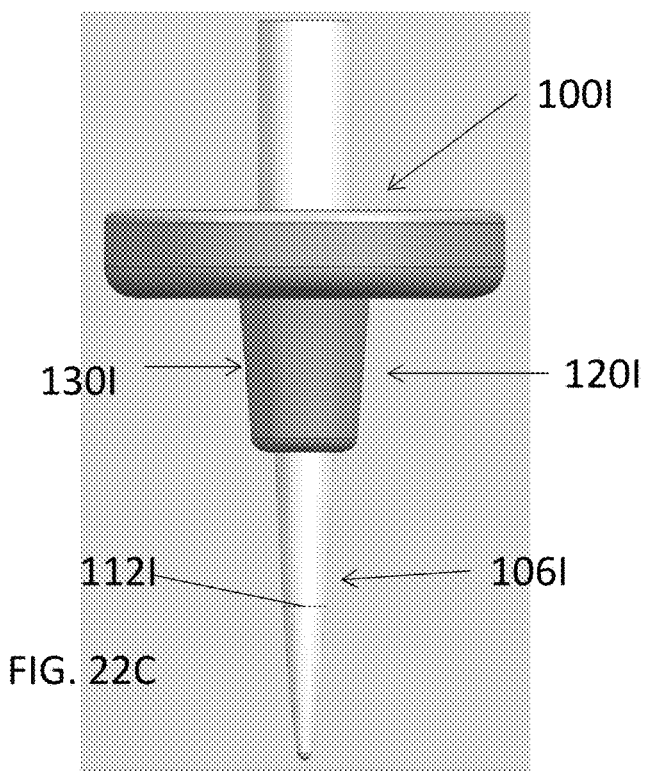
FIG. 22A
FIG. 22B
FIG. 22C

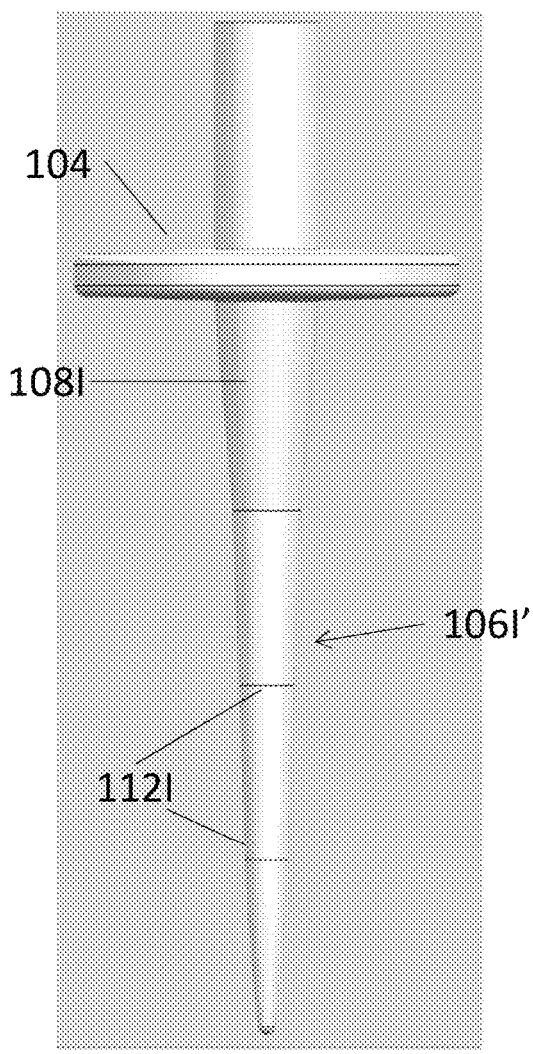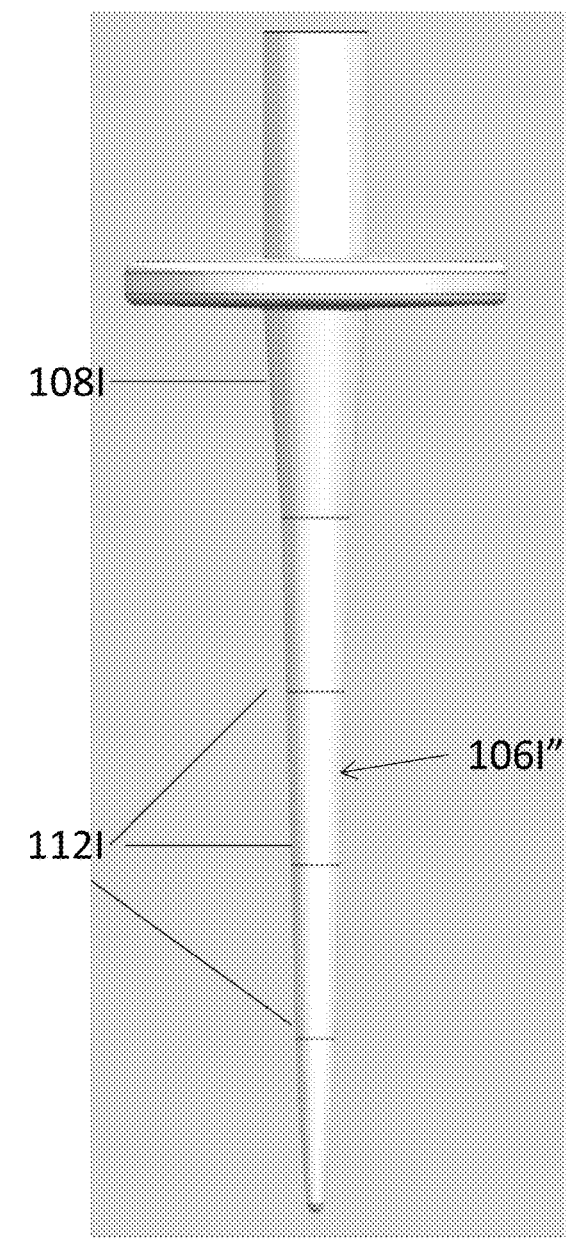
FIG. 22D
FIG. 22E

MEDICAL/DENTAL HANDPIECE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates to medical/dental handpieces, and in particular, to a handpiece adapted to receive a light guide to deliver light into a treatment area (such as a root canal, a prepared cavity in a tooth crown, periodontium, or interdental spaces) to facilitate diagnosis (such as tooth cracks and bone loss) and treatment (such as photodynamic therapy and tooth restoration) of the treatment area. The light guide can be static, in which case it only directs light of a desired wavelength and intensity to the treatment area, or active, in which case it can dynamically (mechanically) activate fluids in the treatment areas.

During photodynamic therapy of a root canal has been proposed. Such treatment includes introducing a photoactive solution to the root canal, and introducing light into the root canal to then activate the photoactive compound in the solution. U.S. Pat. No. 9,987,200, which is incorporated herein by reference, discloses disinfecting a root canal via photodynamic therapy. As described therein, the method comprises introducing a photoactive solution into the root canal, removing excess photoactive solution from the root canal, introducing a micro-bubble solution comprised of an oxygen carrier, an oxidizing agent and a surfactant into the canal, mechanically activating the micro-bubble solution in the canal; and introducing light into the root canal to activate the photosensitive compound in the photoactive solution. Mechanical activation of the micro-bubble solution can be accomplished by inducing sonic or ultrasonic vibrations in a probe or by rotationally or reciprocatingly driving a probe. Mechanical activation of micro-bubble solution generates micro-bubbles which scatter the light introduced into the canal, such that the light will impact, and activate, the photosensitive compound throughout the root canal system, including photosensitive compound that is adhered to biofilm and/or bacteria in dentinal tubules, lateral canals, etc. The activated photosensitive compound releases energy to the oxygen molecules supplied by the micro-bubble solution, converting the oxygen molecules to singlet oxygen (S1 or 1 P*). The singlet oxygen is highly reactive, and destroys the biofilm and bacteria via oxidative damage.

What is needed is a handpiece that can deliver light into a treatment area, such as the root canal and/or periodontium, to activate a photosensitive compound and/or mechanically activate the solution to enhance treatment of the treatment area. In addition, such a handpiece could be used to facilitate diagnosis of, for example, tooth cracks, bone loss, and caries and in the procedures of apical surgeries such as Root End Resections (RER), Root End Preparations (REP), osteotomies and biopsies.

BRIEF SUMMARY OF THE INVENTION

Disclosed herein is a medical/dental handpiece and associated light guides which can be used for both diagnosis and treatment of, for example, dental issues. For example, the handpiece and associated light guides can be used for detection of tooth cracks, locating the orifice at the base of the pulp chamber, locating calcified and/or blocked canals within the roots of teeth, determination of bone loss in the gums, detection of certain cancers, treatment of root canals, caries, and restoration of teeth. Although the handpiece is described below for use with dental procedures, it will be apparent that the device can also be used for medical procedures.

Briefly stated, a medical/dental handpiece, comprises a housing having a head portion, a motor selectively switchable between an activated mode in which its output shaft rotates or reciprocates and an deactivated mode in which its output shaft neither rotates nor reciprocates, an output shaft gear member operatively driven by the motor, a light source comprising at least one or more light producing elements selectively switchable between an activated mode in which the light source produces light, and a deactivated mode in which the light source does not produce light, and a light guide holder mounted in the head of the handpiece for rotation relative to the head. The light guide holder comprises a sleeve and a circumferential flange on the sleeve teeth on an upper surface thereof to define a light guide holder gear. The sleeve further defines a passage therethrough which is axially aligned with an opening in the bottom surface of the head and the light source, whereby when activated, light from the light source will be directed toward the passage of the light guide holder. The light guide holder and the output shaft gear are positioned in the housing such that the output shaft gear drives meshes with the teeth of the light guide holder, such that when the motor is activated, the light guide holder will be driven by the output shaft gear. A light guide comprises a stem and a probe below the stem, the stem being sized to be removably received in the sleeve of the light guide holder such that the light guide will be driven by the light guide holder upon activation of the motor. The light guide being made at least in part of light transmitting material, whereby the light guide receives the illumination from the light source when the light source is activated, and the illumination passes through the light guide stem to exit through the probe of the light guide. Lastly, the handpiece includes a control circuit for the handpiece; the control circuit comprising the motor, the light source, and at least one switch, such that the handpiece is operable in three modes: (1) only the motor is activated, (2) the light source is activated, and (3) both the motor and light source are activated.

In accordance with an aspect of the handpiece, the light source can be a dedicated light source (i.e., to operate at a single wavelength or intensity) or it can be configured to change the wavelength and/or intensity of the light produced by the light source. Whether the light source is a dedicated light source or a variable light source, the light source can comprise a single light producing element or two or more light producing elements.

In accordance with an aspect of the handpiece, the light source comprises a plurality of discrete light producing elements, and the control circuit is configured to selectively activate only one of the discrete light producing elements or selectively activate two or more of the discrete light producing elements. In one variation, the plurality discrete light producing elements include at least two light producing elements which emit light in different wavelengths; and in another variation, the plurality of discrete light producing elements include at least two light producing elements which emit light at the same wavelength.

In accordance with an aspect of the handpiece, the light guide can include a coating at least on walls of the probe. The coating can be a coating which permits no light to pass through the coating or which permits a desired amount of the light to pass through the coating such that light exits the light probe only at desired portions or intensities of the light probe. The coating can be, for example, a silicon coating or a reflective metal coating.

In accordance with an aspect of the handpiece, the light guide can comprise a plate between the stem and the probe which is positioned adjacent an outer surface of the bottom surface of the head when the light guide is received in the light guide holder. The handpiece can further comprise a cover comprising an attachment portion adapted to be connected to the plate of the light guide and a nose which extends from the attachment portion; the nose at least in part surrounding the probe.

In accordance with an aspect of the handpiece, the cover is made from a flexible and conformable material such that when pressed against a surface; the protective sleeve will conform to the shape of the surface.

The probe can have different configurations. For example:
the probe can taper along a length of the probe and be sized to extend into a prepared root canal, an access cavity, clinical crown or a periodontal pocket adjacent a tooth.
the probe can include at least one measurement marking along the length of the probe.
the probe can be shaped to mechanically activate fluid in a root canal or cavity upon activation of the motor.
the probe can be generally cylindrical in cross-section.
the probe can include an end portion on a distal end of the probe, wherein:
the end portion comprises a prism having an end surface in the form of a polygon and side surfaces extending from edges of the end surface to the distal end of the probe.
the end portion is sized and shaped to be received in spaces between teeth or in periodontal pockets.
the end portion comprises a triangular prism extending from the distal end of the probe.
the probe can define an upper section and a lower section, wherein, the lower section angles away from the upper section.

In accordance with an aspect of the handpiece, the nose of the cover can extend substantially the full length of the probe, such that substantially only the end portion of the probe extends beyond the nose, such that light exits substantially only through the end portion.

In accordance with an aspect of the handpiece, the probe has a diameter sized to enable the probe to extend into a tooth root canal.

In accordance with an aspect of the handpiece, the probe has a diameter sized such that cover will engage and cover an upper surface of a tooth when the probe is positioned on a tooth.

In accordance with an aspect of the handpiece, the handpiece further comprises an output shaft extending from the motor, the output shaft gear being at an end of the output shaft spaced from the motor; the output shaft being rotatable about an output shaft axis; and wherein the light guide holder is rotatable about a light guide holder axis that is offset from the output shaft axis.

In accordance with an aspect of the handpiece, the handpiece comprises a first bearing surface and a second bearing surface in the head of the handpiece. The first bearing surface defines an arc in a plane generally perpendicular to the output shaft axis; the output shaft gear member defines a shoulder which rotates against the first bearing surface; and the second bearing surface being generally cylindrical and being sized to rotatably receive an upper portion of the sleeve of the light guide holder.

In accordance with an aspect of the handpiece, that handpiece includes a gear cover received in the head of the handpiece, wherein the gear cover defines the first and second bearing surfaces. The gear cover has an upper surface defining an opening aligned with the sleeve of the light guide holder; the light source being positioned to direct illumination through the opening.

In accordance with an aspect of the handpiece, that handpiece includes a gear box assembly positioned between the motor and the output shaft, wherein the torque reduction assembly comprises a plurality of intermeshing gears which reduce a torque and increase speed output by the motor to a desired torque and speed.

In accordance with an aspect of the handpiece, the handpiece comprising:
a housing having a base portion, a central portion, distal portion, and a head portion at an end of the distal portion; the head portion having a bottom surface defining an opening;
a motor contained within the housing;
an output shaft operatively connected to the motor to be driven by the motor; the output shaft rotatable about an output shaft axis;
an output shaft gear rotationally fixed to the output shaft to be driven by the output shaft, wherein the output shaft gear comprises a distal gear portion,
a light guide holder rotatably mounted in the head; the light guide holder comprising a hollow sleeve defining a passage therethrough, a circumferential flange on the sleeve having teeth on an upper surface of the flange to define a light guide holder gear; the light guide holder gear being positioned in the head such that the sleeve is axially aligned with the opening in the bottom surface of the head; the light guide holder being rotatable about a light guide axis which is offset from the output shaft axis;
a first bearing surface and a second bearing surface in the head of the handpiece; the first bearing surface defining an arc in a plane generally perpendicular to the output shaft axis; the output shaft gear defining a shoulder which rotates against the first bearing surface; and the second bearing surface being generally cylindrical and being sized to rotatably receive an upper portion of the light guide holder sleeve; the first and second bearing surfaces positioning the output shaft gear and the light guide holder gear such that they mesh, wherein the light guide holder gear is rotationally driven rotationally by the output shaft gear; and
a light source positioned in the handpiece, the handpiece being configured to direct light into the light guide holder sleeve when the light source is activated.

In accordance with an aspect of the handpiece, the first and second bearing surfaces are defined by a gear sleeve cover; the gear cover having an upper surface defining an opening aligned with the sleeve of the light guide holder; the light from the light source being directed through the opening.

In accordance with an aspect of the handpiece, the light guide holder is driven by the output shaft gear about an axis that is distinct from the axis of the output shaft gear.

In accordance with an aspect of the handpiece, the light guide holder is driven rotationally and/or reciprocatingly.

BRIEF DESCRIPTION OF THE DRAWINGS

FIG. 11 is a perspective view of a light guide receiving gear member which is mounted in the head of the handpiece;

FIGS. 12A-12D are top perspective, front elevational, bottom plan, and top plan views of a gear sleeve cover of the handpiece;

FIGS. 20A-B are elevational and bottom perspective views, respectively of a seventh light guide;

FIG. 20C is an elevational view of the seventh light guide with an associated shield;

FIGS. 22A-B are elevational and bottom perspective views, respectively of an ninth light guide;

FIG. 22C is an elevational view of the ninth light guide with an associated shield; and FIGS. 22D-E are elevational views of variations of the ninth light guide.

Corresponding reference numerals will be used throughout the several figures of the drawings.

DETAILED DESCRIPTION

Figure 1:
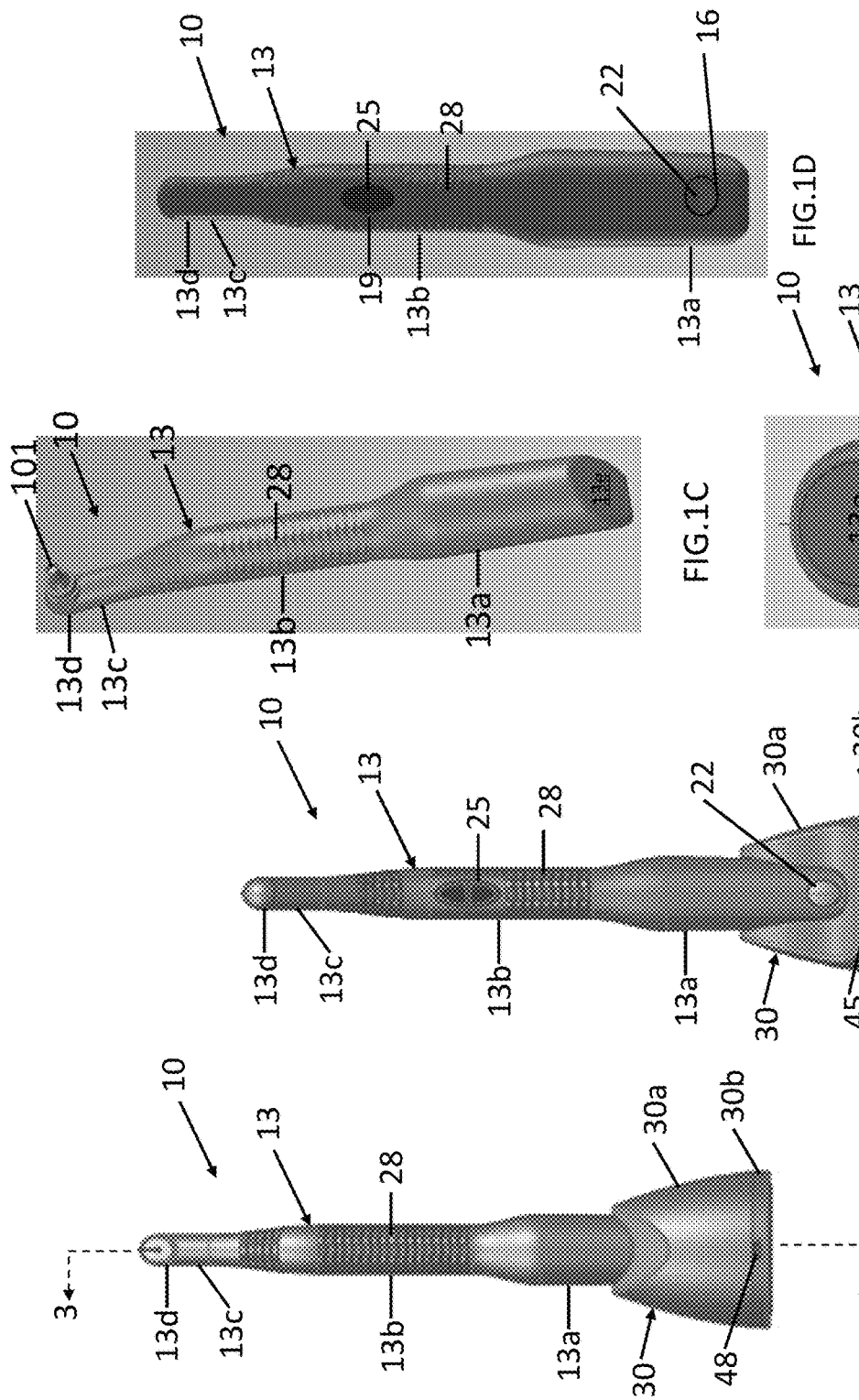
FIG. 1A is a front elevational view of an endodontic handpiece with a light guide mounted in a head thereof and set in a charging base.
FIG. 1B is a rear elevational view of the handpiece in the charging base.
FIG. 1C is a perspective view of the handpiece with a light guide mounted in the head.
FIG. 1D is a rear elevational view of the handpiece.
FIG. 1E. is a bottom plan view of the handpiece.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Figure 2:
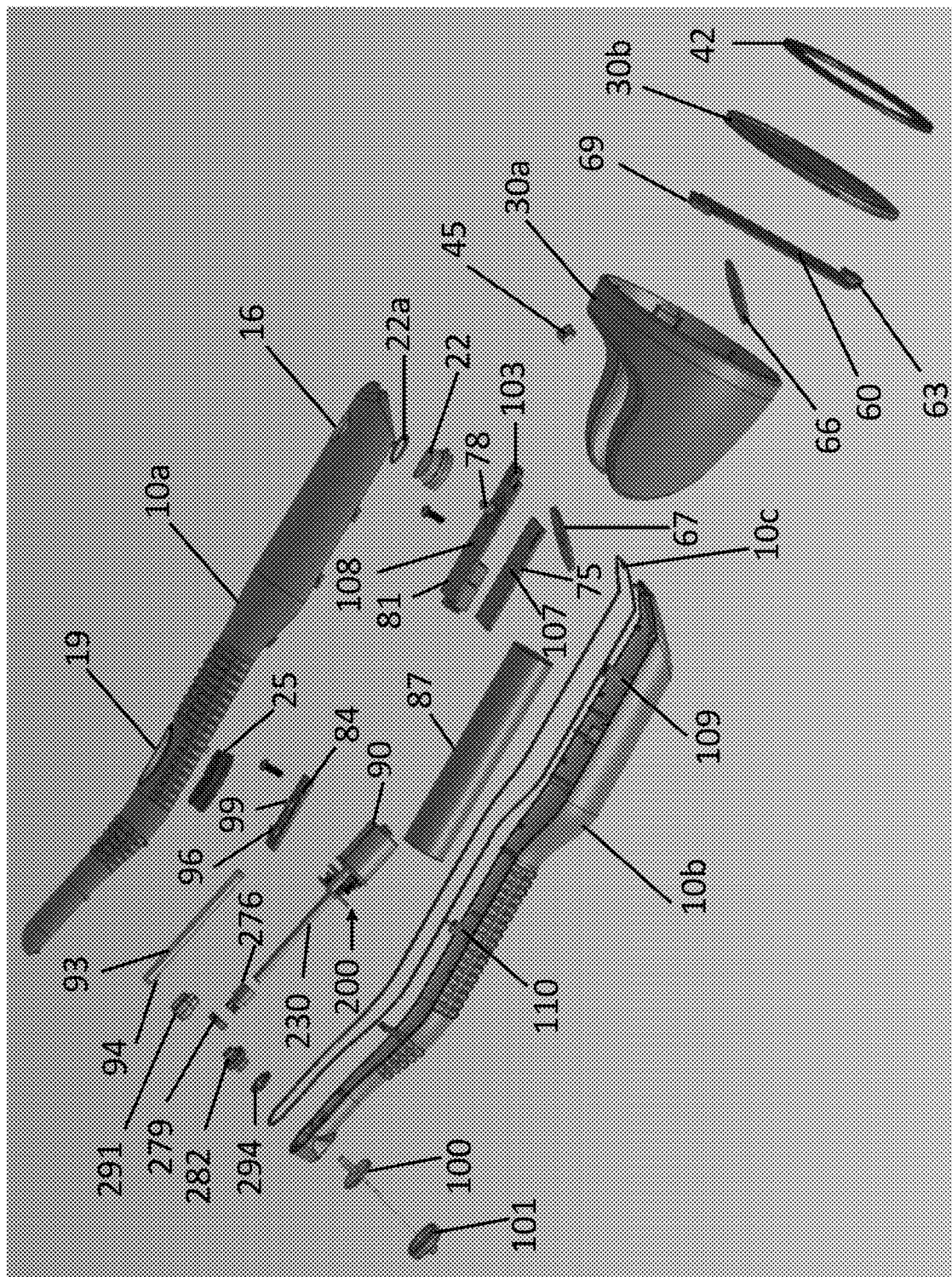
FIG. 2 is an exploded perspective view of the handpiece and charging base.

An illustrative embodiment of the handpiece 10 set in a charging base 30 is shown in FIGS. 1A-B, and free of the charging base in FIGS. 1C-E. The handpiece 10 comprises a housing or shell 13 defining a base portion 13a, a central portion 13b at an end of the base portion, and a distal portion 13c at the end of the central portion, the distal portion defining a head 13d of the handpiece. The housing 13, as seen in FIG. 2 is comprised of a top shell 10a and a bottom shell 10b, which are connected together in any desired manner. For example, they can snap together. A compressible seal 10c is positioned between the top shell 10a and the bottom shell 10b to provide a fluid-tight and air-tight seal between the top and bottom shells to prevent moisture, dust, and other particles from entering the interior of the shell 13.

The base portion 13a of the handpiece is generally circular, defining a radius larger than the radii of the central and distal portions of the handpiece 10. However, the base portion 13a may have any shape that is conducive to proper operation of the endodontic handpiece. As will become apparent, the base portion 13a defines a charging and battery storage region of the handpiece 10. Near the bottom of the base portion 13a, the top shell 10a includes a hole 16, which receives a light window 22 (FIG. 1D). An O-ring 22a (FIG. 2) forms a seal between the light window 22 and the opening 16 in the housing 13. The handpiece also includes an electrical charging port opening 23.

The central portion 13b of the handpiece 10 extends forwardly or upwardly from the base portion 13a. The base portion slopes inwardly at its bottom and sides, to meet the bottom end of the central portion. The central portion 13b, as noted, defines a diameter smaller than the diameter of the base portion 13a. Although an axis of the central portion is generally parallel to an axis of the base portion, the central portion 13b is not coaxial with the base portion. Rather, the axis of the central portion is offset from the axis of the base portion, as can best be seen in FIG. 3, such that the top surfaces of the base and central portions define a continuous and generally straight line. The central portion 13b has a textured gripping area 28 which is shown to extend around the circumference of the central portion. Toward the distal end of the central portion 13b, the top shell 10a includes an elongated hole 19 (FIG. 2) that receives a switch cap 25.

Figure 3:
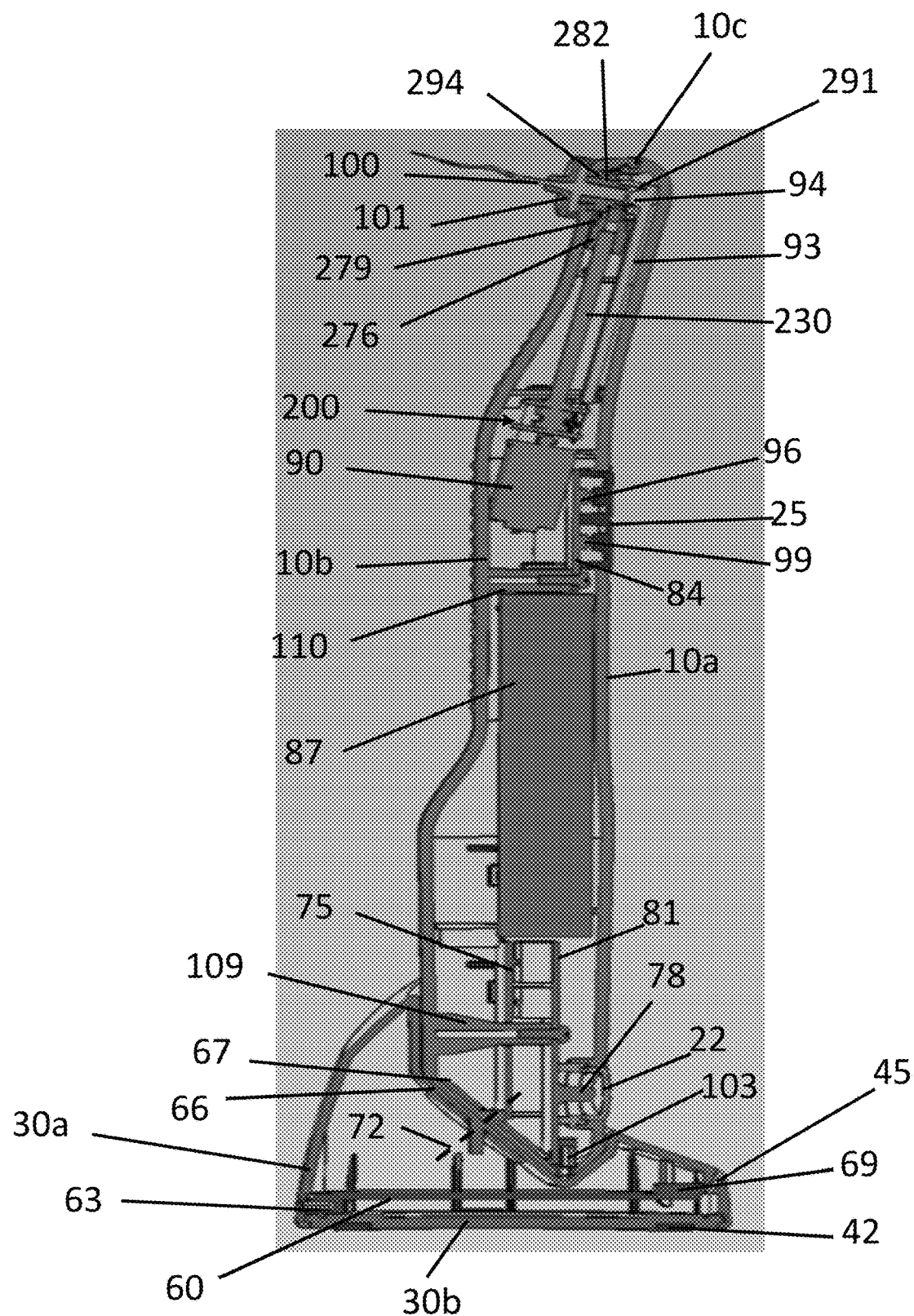
FIG. 3 is a cross-sectional view of the handpiece and charging base taken along line 3-3 of FIG. 1A.
Figure 4A:
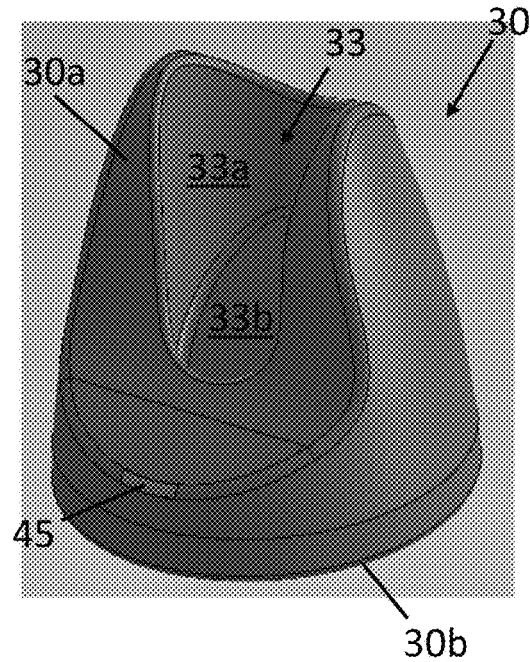
FIG. 4A is a front perspective view of the charging base.
Figure 4B:
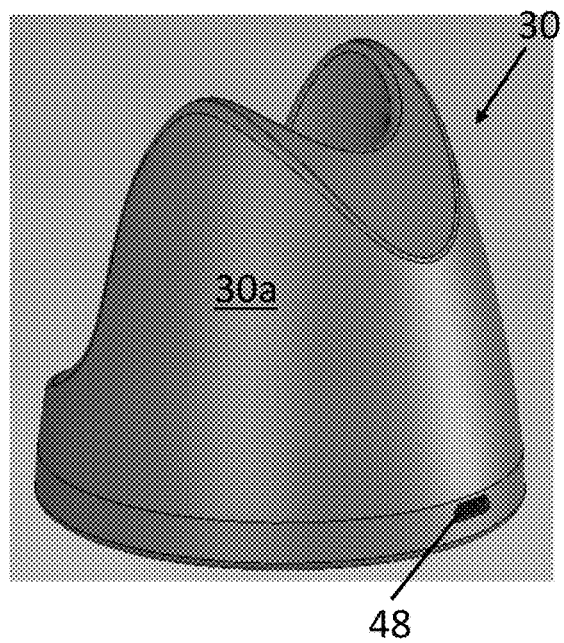
FIG. 4B is a rear perspective view of the charging base.
Figure 4C:
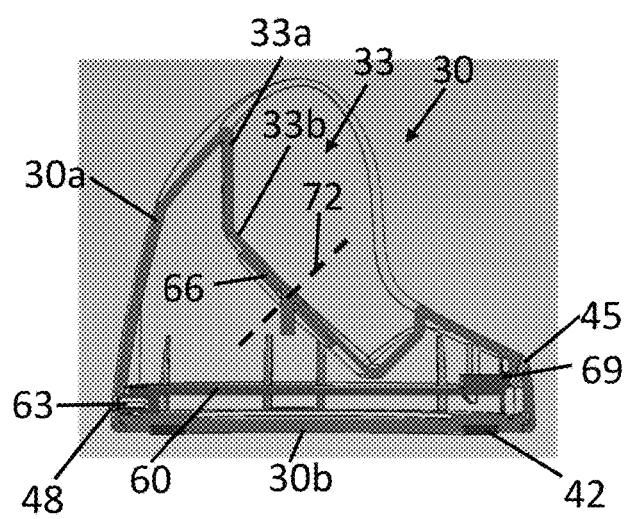
FIG. 4C is a cross-sectional view of the charging base.
Figure 4D:
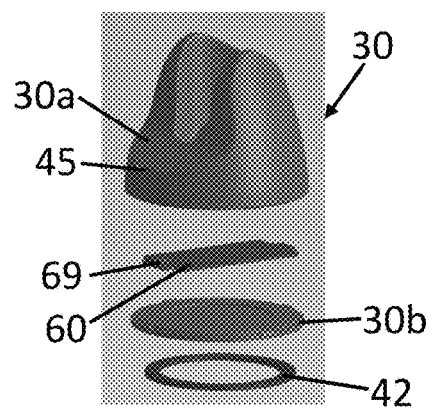
FIG. 4D is an exploded view of the charging base.

The distal portion 13c of the handpiece 10 extends from the central portion 13b. Although an axis of the distal portion 13c could be parallel to the axis of the central portion 13b (such that the hand piece would be generally straight), the distal portion 13c angles upwardly from the central portion 13b, as seen in FIG. 3. As such, the handpiece has the configuration of a contra-angle often used in dental practices. The distal portion 13c, as noted, defines a head 13d at its distal end. The head 13d has a bottom surface which, in turn, defines an opening sized to receive a stem of a light guide, as described below. The bottom surface of the head is preferably flat but could define a curved surface if desired. The bottom surface of the head is generally parallel to the top surface of the handpiece distal portion, as seen, for example, in FIG. 3.

Turning to FIGS. 4A-D, the charging base 30 comprises a base housing 30a and separate bottom member 30b, which are connected together in any desired manner. The charging base 30 defines an upwardly opening charging cavity 33 that is sized to receive the base portion 13a of the handpiece 10. The charging cavity 33 is defined by a support wall 33a and a floor 33b. The charging cavity is shaped complimentary to the handpiece base portion 13a to be able support the handpiece 10 in a generally vertical orientation when the handpiece is placed in the charging base. The support wall 33a preferably does not extend fully around the handpiece, such that the charging cavity 33 opens to the front of the base 30. This opening exposes the base portion 13a of the handpiece 10 when it is received by the charging cavity 33, such that that light window 22 is visible, as seen in FIG. 1B. The floor 33b of the charging base 30 is configured to be generally parallel to the end surface 13e of the base portion 13a of the handpiece 10 when the handpiece is received in the base. The end surface 13e of the handpiece is angled (i.e., it is not perpendicular to the side walls of the base portion). The floor 33b of the charging cavity 33 is thus similarly sloped. As described below, the handpiece 10 and base 30 are formed such that the handpiece end surface 13e and the charging cavity floor 33b are in abutting relationship when the handpiece is received in the charging base. Although the handpiece end surface 13e and charging base floor 33b are shown to be generally planer, they may be formed in any desired fashion, and can alternatively be flat (i.e., normal to the walls of the handpiece base portion 13a), or curved.

A light window 45 is formed in the charging base 30 below the bottom of the opening to the cavity 33 of the charging base 30. The light window 45 is shown as elongate, but may be any desired shape. The window 45 allows for light from an internal charging indicator light 69 (FIG. 4C), such as an LED, to be visible, so that it is easily determined that the charging base is in operation.

A charging port opening 48 is formed at the bottom of the charging base 30, preferably in the back of the base. The charging port opening 48 is formed to receive the distal end of a charging cord to connect the charging base 30 to a source of power.

A ring 42 made of a flexible rubber or silicone material is adhered to the bottom surface 30c of the lower portion 30b of the charging base 30, thereby effectively forming a resting surface for the charging station.

The housing 30a and the bottom member 30b define a hollow space in which is contained the electronic components that are designed to facilitate charging (and preferably wireless inductive charging) of the handpiece 10. Internally, the charging base 30 comprises a charging circuit board (PCB) 60 supported in and positioned to be aligned with the charging port opening 48 and the light window 45. The charging PCB 60 includes a cable receiver 63 aligned with the charging port 48 and which is designed to receive a connector or plug of any standard type of charging cord. For example, the charging cord can be a USB (-A, -B, or -C) charging cord, a micro-USB charging cord, a mini-USB charging cord, a pin-type charging cord, a Lightening® charging cord, or any other connector that is capable of providing power to the charging base 30. The circuitry on the charging PCB 60 receives the charging current through the charging cable receiver 63 from the exterior charging cable which has a distal end adapted to be connected to a source of electricity. The circuitry is capable of energizing an inductive charging coil 66 contained within the charging base 30 and positioned adjacent the underside of the floor 33b of the charging cavity 33. The charging coil 66 is centered about an axis 72 passing through the center of, and perpendicular to, the floor 33b of the cavity 33. The coil 66 is electrically connected to the charging PCB 60. Thus, the inductive charging coil 66 facilitates inductive charging of the handpiece when the handpiece is received in the base and the base is connected to a source of electricity.

The charging PCB 60 also includes a charging indicator light 69 (such as an LED or series of LEDs) that is activated when charging PCB 60 is connected to a source of electricity via the charging cable. The charging indicator light 69 is aligned with, and visible through, the light window 45 below the opening to the cavity 33. In this position, the light is positioned to transmit through the window 45 of the charging base 30. The light 69 is controlled by the PCB 60 to show three distinct modes of operation. In the first, 'OFF' mode, the light 69 is not illuminated and thus, inductive charging is not taking place. In the second, 'CHARGING', mode, the light 69 flashes (for example, in red) indicating that charging is actively taking place. In the third, 'CHARGED', mode, the light 69 displays continuously (i.e., the light is not flashing) indicating that the handpiece 10 is fully charged. The color displayed in the CHARGED mode can be a different color from the CHARGING indicator. For example, the CHARGED indicator can, for example, be white or green. The three modes (OFF, CHARGING, and CHARGED) can be displayed via the light 69 in any other desired manner. What is preferred is that the light display be different for the three modes, so that the mode of operation is easily determined. The light displayed by light 69 through the window 45 can be different colors and/or different patterns.

For wireless charging to take place, the handpiece 10 must be received in the charging cavity 33 of the charging base 30, with the end surface 13e of the handpiece base adjacent the floor 33b of the charging cavity. When energized, the inductive charging coil 66 of the charging base will create a magnetic field. The magnetic field will encapsulate and surround the inductive charging coil 66, and is capable of interacting with any material that is exposed to this field.

With reference to FIG. 3, a second inductive charging coil 67 is positioned on the end surface 13e in the interior of the housing 13. When the base end 13a of the handpiece 10 is received in the charging cavity 33, the second inductive charging coil 67 interacts with the induced magnetic field created by the inductive charging coil 66 positioned on the interior of the charging base 30. The interaction with the magnetic field induces an electric current in the second inductive charging coil 67.

The base portion 13a of the handpiece contains two control boards. A power control PCB 75, positioned in the hollow interior of the housing 13, is electrically connected to the winding coil 66 and comprises the required circuitry for charging of a battery 87 contained within the handpiece 10. As seen in FIG. 3, the battery 87 extends from the base portion 13a into the central portion 13b.

A second control PCB 81 is positioned adjacent the power control PCB 75. The second control PCB 75 comprises the Main Control Unit (MCU) which manages the operation of the handpiece 10. The MCU may take on the form of a field-programmable gate array (FPGA) or a microcontroller and is programmed to control all of the functional capabilities associated with operating the handpiece 10.

An operational light 78 and a charging port 103 are positioned on the power control PCB 81 to be aligned with the light window 16 and the charging port opening 23, respectively. The power control PCB 81 is positioned within the base portion 13a of the handpiece such that the operational light 78 and the charging port 103 are aligned with their respective windows/openings 22 and 23. The charging port 23 can, for example, accept a micro-USB cord. Although, the handpiece is preferably used as a cordless handpiece, the provision of the charging port 103 allows for the handpiece to be used in a corded manner if it is not fully charged. Alternatively, the charging port 103 can be used to connect an external or supplemental battery to the handpiece to allow the handpiece to be used in a cordless manner when the internal battery no longer has sufficient charge. As can be appreciated, such an external or supplemental battery would preferably be formed in a manner that would allow it to be connected to the handpiece, and such that it would not interfere with the ergonomics of the handpiece.

When the handpiece 10 is positioned in the charging cavity 33 for charging, the power control PCB 75 will transmit the charging current to the second control PCB 81, where the MCU will either pass the current to the battery 87 for charging, or block the current if the battery 87 is already charged to full capacity. The MCU also has the capability of determining the operational status of the handpiece and sending an indication message to the operational light 78. The indication message will trigger any of a set of status indicator colors that will be illuminated by the operational light 78.

The battery 87 is positioned in the hollow interior of the handpiece 10. The battery 87 is positioned towards the distal end of the power control PCB 75 and the second control PCB 81 and extends from the base portion 13a into the central portion 13b of the handpiece 10. The battery 87 is electrically connected to the PCBs 75 and 81 so as to be charged when the handpiece is positioned in the charging base 30 and to provide power to the handpiece when in use.

A switch PCB 84 is positioned in the hollow interior of the handpiece central section 13b proximate the elongated hole 19 in the top shell 10a. The switch PCB 84 is electrically connected to the battery 87 and the second control PCB 81. The switch cap 25 is positioned above the switch PCB 84 and extends through the elongated hole 19 in the top shell 10a. The switch cap 25 is shown to be an elongated oval, but can be rectangular or any other desired shape. The switch PCB 84 has a light switch 96 and a motor switch 99 positioned thereon that are capable of receiving an on/off input from the switch cap 25 when depressed. The light and motor switches 96, 99 are positioned on the PCB 84 to be below opposite ends of the switch cap 25. The switch cap, in turn, is mounted to be selectively movable between positions in which (1) only the light switch 96 is depressed, (2) both the light and motor switches are depressed; (3) only the motor switch is depressed; and (4) neither the light nor the motor switch are depressed. Thus, a single control element (i.e., the switch cap 25) controls both a motor and light of the handpiece, to allow the motor and light to be used in combination or independently of each other.

A light PCB 93 is electrically connected to the switch PCB 84 to be activated when the light switch 96 is depressed. The light PCB 93 extends along the distal portion 13c of the handpiece 10 ending in the distal head portion 13d of the handpiece. The light PCB 93 comprises a light source 94 positioned at its distal end that its oriented to direct light toward the bottom surface of the head 13d. One of the control boards (such as any of PCB 75, 81, or 93) can include a timer circuit or timer logic, which activates the light source for a determined period of time after the light switch is depressed. The light source 94 is preferably an LED, and more preferably, a series of LEDs of different colors. For example, the light PCB can include 4 LEDs—red, green, blue, and white. Further, if desired, the PCB 93 can include multiple LEDs of the same color (for example, the PCB 93 can include two red LEDs). Although LEDs are disclosed, the light energy can be generated using any other desired light source. For example, the light source could be a laser. All that is necessary is that the emitted light be in of a wavelength and intensity desired for the function to be performed by the light (i.e., activate a photosensitive compound, cure filling material, or provide visible light to allow for visual inspection of a treatment area). The light PCB 93, and thus the light source 94, is activated by moving (sliding, pressing, or toggling) of the switch cap 25 to depress the light switch 96. Preferably, the PC boards are programed such that an on/off signal is received from the switch PCB when the light switch 96 is pressed for a duration of greater than two seconds to activate (or deactivate) the light source 94.

In an alternative, the light PCB 93 and the light source 94 may be operable to alter the wavelength of the emitted light emitted to easily change between, for example, a wavelength intended for visual inspection and a wavelength intended for curing filing material. This would eliminate the need for multiple LEDs to provide light of different wavelengths. However, such a board could include multiple LEDs to facilitate changing the intensity of the transmitted light.

In an embodiment, the light PCB 93 is capable of controlling the color of light that is illuminated from the light source 94. When the light switch 96 is pressed for a short duration, the light control circuitry cycles the light source between a predetermined set of colors; for example, the light source 94 can cycle through the colors white, green, blue and red. For example, when the light switch 96 is pressed and quickly released, the light source will be changed to the next preprogrammed color. This can be accomplished using multiple LED's, as discussed above. Alternatively, a single light source can be used which is capable of changing color in response to a change in input. In another alternative, the handpiece can be provided with filters which allow only selected colors to pass through. In this instance, repeated pressing of the light switch will select different filters through which the light will be directed. Further, the light source 94 can be operated to activate two or more LEDs together. For example, the red and blue LED can be activated simultaneously. Alternatively, if the PCB 93 includes multiple LEDs of the same color, the intensity for that particular color can be significantly increased by activating the multiple LEDs of the same color. For example, if the light PCB included two red LEDs, the handpiece could be operate to activate both red LEDs to increase the intensity of red light. Intensity can also be accomplished in a handpiece with a single light source by using a dimmable light source, such that the light intensity changes in response to an input, such as from a rheostat or other switching circuitry that will change the intensity of a single light source. The ability to change the color (i.e., wavelength) and/or the intensity of the light source 94 broadens the uses of the handpiece and enables the handpiece to be used to activate solutions with photoactive compounds or nanoparticles, cure compounds (such as for pre- and post-endodontic restorations), transilluminate hard and soft tissue (such as tooth, bone, and gum tissue) to detect tooth cracks, bone loss, and certain cancers by chemiluminescence.

Figure 8A:
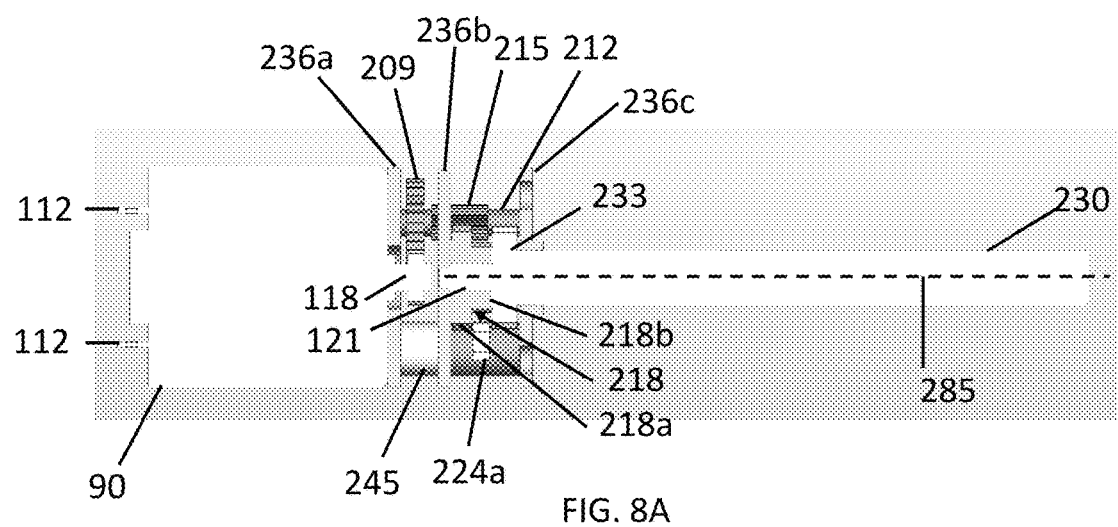
FIGS. 8A, 8B, and 8C are cross-sectional views of the gear box assembly along a direction parallel to the axis of the motor output shaft, taken along parallel planes passing through different driven shafts of the gear box assembly.
Figure 8B:
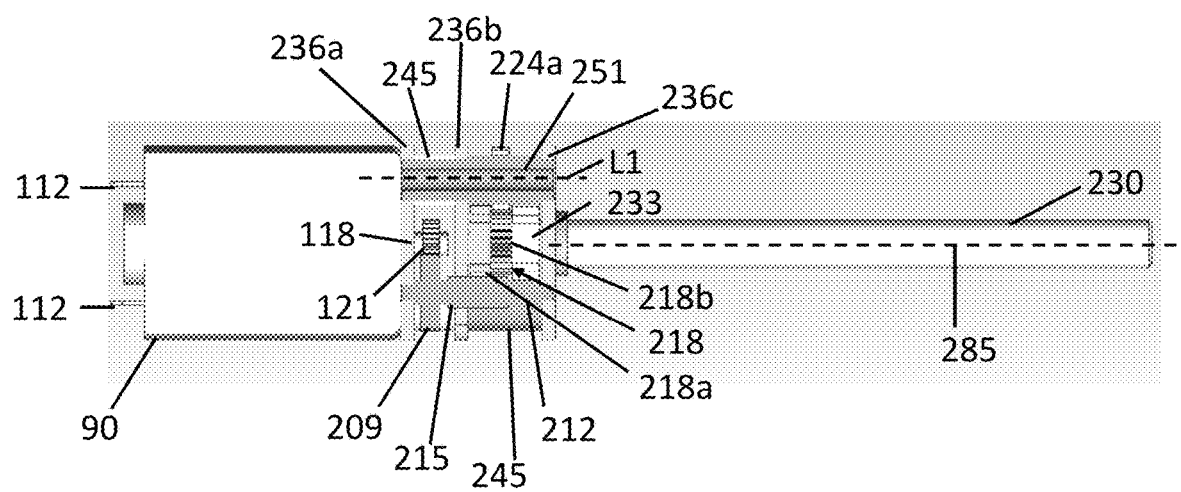
Figure 8C:
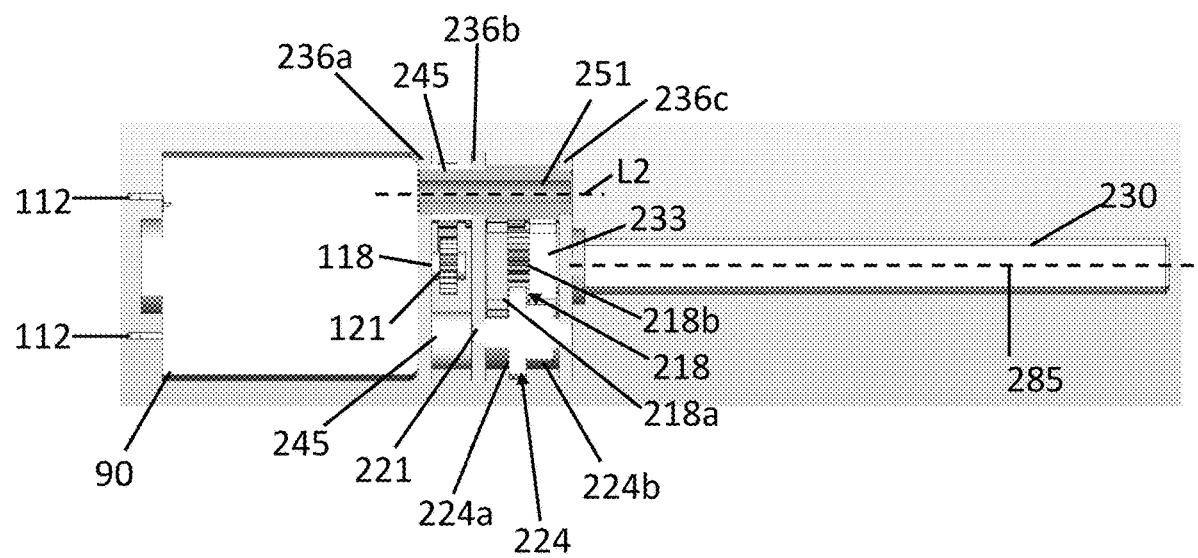

A motor 90 is positioned at the forward end of the central portion 13*b* of the housing. The motor 90 includes electrical terminals 112 which electrically connect the motor 90 to the PC board 81, which controls activation of the motor in response to the position of the motor switch 99. A motor output shaft 118 (FIG. 8A) extends from the distal end of the motor 90. In the illustrative embodiment shown, a motor output gear 121 on the output shaft 118 drives a gear box assembly 203 which in turn drives a driven output shaft 230 that extends forwardly to the head of the handpiece. The output shaft can be driven to rotate or reciprocate (i.e., alternate between clockwise and counter-clockwise motion). If desired, the PCB 81 could be programmed to select between rotational and reciprocal motion in response to signals from the motor switch 99. A timing circuit/logic can also be used to control the motor, such that the motor drives the output shaft 230 rotationally or reciprocatingly for a desired period of time. Alternatively, the time circuit/logic can alternate between driving the output shaft rotationally and reciprocatingly. Finally, the timer circuit/logic can control the light source and motor in combination, such that the light source is activated for a determined period of time before or after the motor is activated for a determined period of time. Or, the light source and motor can be activated simultaneously, and each could be activated for the same amount of time or for different amounts of time.

As discussed below, the output shaft 230 drives (imparts its motion to) a light guide when the light guide is received in the handpiece and the motor is activated. The gear box assembly 203 serves to increase the torque and reduce the rotational speed of the driven output shaft 230 relative to that of motor output shaft 118. Although a mechanical gear box assembly is disclosed, it will be appreciated that the motor 90 could be a single constant- or single-speed motor which produces the desired output torque/rotational speed. Alternatively, motor 90 could be a variable speed motor, and the rotational speed and torque of the motor could be controlled, for example, by means of a speed/torque selector switch or a rheostat. In such an instance, the handpiece could be provided with a speed indicator (such as a light display or an LED digital readout screen) which indicates a relative speed of the motor. For example, the handpiece could have four LEDs visible on the handpiece, with the number of LED's illuminated increasing as speed increases. Alternatively, the handpiece could have a single light which blinks, with the blink rate being indicative of the speed.

With reference to FIGS. 7A-9F, the gear box assembly 203 comprises a series of intermeshing gears that will increase the output torque of the motor (which, for example, can be about 0.114 N-cm) up to about 6.9 N-cm when the motor is operated under unrestricted use. The gear box assembly 203 comprises a first driven gear 209 which meshes with, and is driven by, the motor output gear 121. The first driven gear 209 is mounted on a first driven shaft 212. A pinion gear 215 is positioned concentrically with the first driven gear 209 on the first driven shaft 212. The pinion gear 215 has a radius smaller than that of the first driven gear 209. The pinion gear 215 and the first driven gear 209 are mounted to rotate together. Either they can both be rotationally fixed to the first driven shaft 212, or they can be interconnected (or even be a unitary assembly) and can rotate about the first driven shaft 212. In either event, rotation of the first driven gear 209 by the motor 90 will rotate the pinion gear 215.

The pinion gear 215 meshes with and drives a first gear set 218. The first gear set 218 is rotatably mounted in the gear box assembly on a second driven shaft 221 that is generally parallel to the first driven shaft 212. The first gear set is spaced axially from (forwardly of) the first driven gear 209. The first gear set 218 comprises a driven portion 218*a* and a driving portion 218*b* above the driven portion. The driven portion 218*a* has a larger radius than the driving portion 218*b*. The driven portion 218*a* meshes with, and is driven by, the pinion gear 215. Because the pinion gear is smaller in radius that the first drive gear 209, the first gear set 218 will rotate at a rotational speed less than that of the motor output shaft. The first gear set 218 can be formed as a monolithic piece with a step down in radius from the driven portion 218*a* to the driving portion 218*b*. Alternatively, the two gears of the gear set 218 can be separate gears which are keyed to the second driven shaft 221 or to each other so that they rotate together. When driven by the pinion gear 215, the driven portion 218*a* and the driving portion 218*b* of the first gear set 218 are driven at the same rotational speed. The step down in radius will further decrease the output rotational speed of the gear box assembly while simultaneously increasing the output torque.

The driving portion 218*b* of the first gear set 218 drives a second gear set 224 mounted on a third driven shaft 227. The second gear set 224 is designed similarly to the first gear set in that it comprises a driven portion 224*a* and a driving portion 224*b*. As with the first gear set 218, the driven portion 224*a* and the driving portion 224*b* of the second gear set 224 can be formed as a monolithic piece or as separate gears that are keyed to the third driven shaft or to each other so that they rotate together. The driven portion 224*a* of the second gear set meshes with the driving portion 218*b* of the first gear set, such that rotation of the first gear set 218 will rotationally drive the second gear set 224. The two gears 224*a, b* of the second gear set will be driven at the same rotational speed. However, the driven portion 224*a* of the second gear set 224 has a larger radius than the driving portion 224*b*, which will further reduce the output rotational speed of the gear box assembly while increasing output torque that is delivered.

The driven output shaft 230, as seen, is concentric with, and rotates about the same axis as, the motor output shaft 118 and the second driven shaft 221. The driven output shaft 230 comprises a base end and a distal end and has a driven output gear 233 fixed to its base end. The driven output gear 233 meshes with, and is driven by, the driving portion 224*b* of the second gear set 224. The driven output gear 233 can be mounted to rotate about on the second driven shaft 221, and the output shaft 230 can be fixed to the driven output gear 233 to be rotatably driven. In this instance, the driven output gear 233 receives the base of the output shaft 230. Alternatively, the driven output shaft 230 can be an extension of the second driven shaft 221. For this purpose, the first gear set 218 (which is mounted on the second driven shaft 221) would need to be mounted to rotate relative to the second driven shaft 221, and the driven output gear 233 would need to be keyed to the output shaft 230/second driven shaft 221 to drive the output shaft.

The driven output gear 233 of the driven output shaft 230 meshes with, and is driven by, the driving portion 224*b* of the second gear set 224. When the second gear set 224 is driven by the first gear set 218, the driving portion 224*b* of the second gear set 224 meshes with and transfers rotational energy to rotate the driven output gear 233. The driven output gear, fixed concentrically with the driven output shaft 230, will be driven by the driving portion 224*b* of the second gear set 224 with a lower rotational speed and increased torque relative to the initial rotational speed and torque of the motor output driving shaft 118 and the motor output gear 121. As the driven output gear 233 is driven by the driving portion 224*b* of the second gear set 224, the driven output shaft 230 is driven rotationally via the driven output gear 233. The rotational speed and torque that are delivered to the driven output gear 233 are transferred directly to the driven output shaft 230. When the motor 90 is activated, the rotational speed and torque will be transferred through all of the gears in the gear box assembly 203, to finally drive the driven output shaft 230 at a predefined rotational speed and torque.

The three gear sets (215, 218, 224) collectively create an increase in torque of between 50 and 70 times and a decrease in rotational speed relative to the torque and rotational speed of the motor 90. The final output in torque is sufficient to drive the output shaft 230 at an appropriate rotational speed for activating disinfecting solutions within the root canal. The torque that is delivered to the driven output shaft 230 is in the range from 6 N-cm to 8 N-cm when the shaft 230 is unrestricted. When the shaft 230 is restricted, the output torque can range from 1 N-cm to approximately 5 N-cm.

The gears can be made of a plastic or a metal. If the gears are made of metal, the handpiece can further be used to drive, for example, dental files and dental burs used to shape canals and drill teeth or drill bits for use in drilling into bone, etc.

Figure 9A:
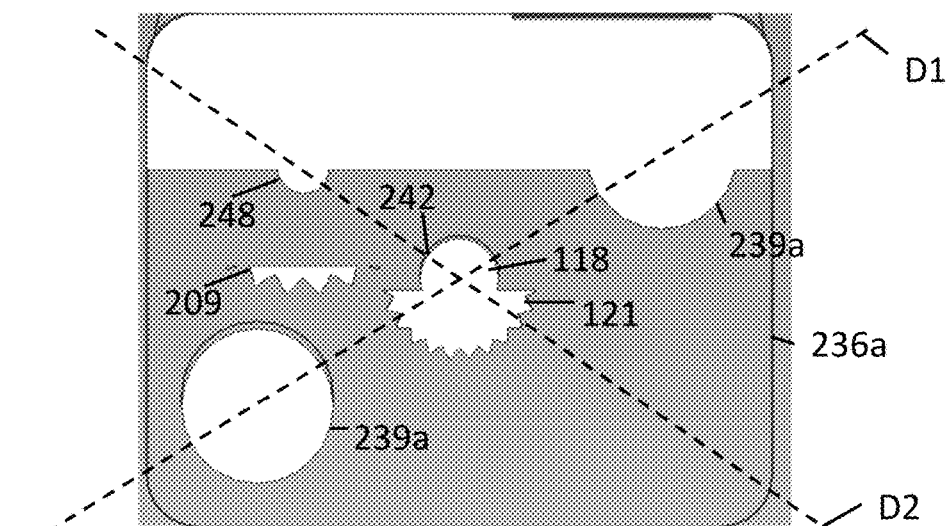
FIG. 9A is a cross-sectional view of the gear box assembly taken along line A-A of FIG. 7B looking rearwardly at a first plate of the gear box assembly.
Figure 9B:
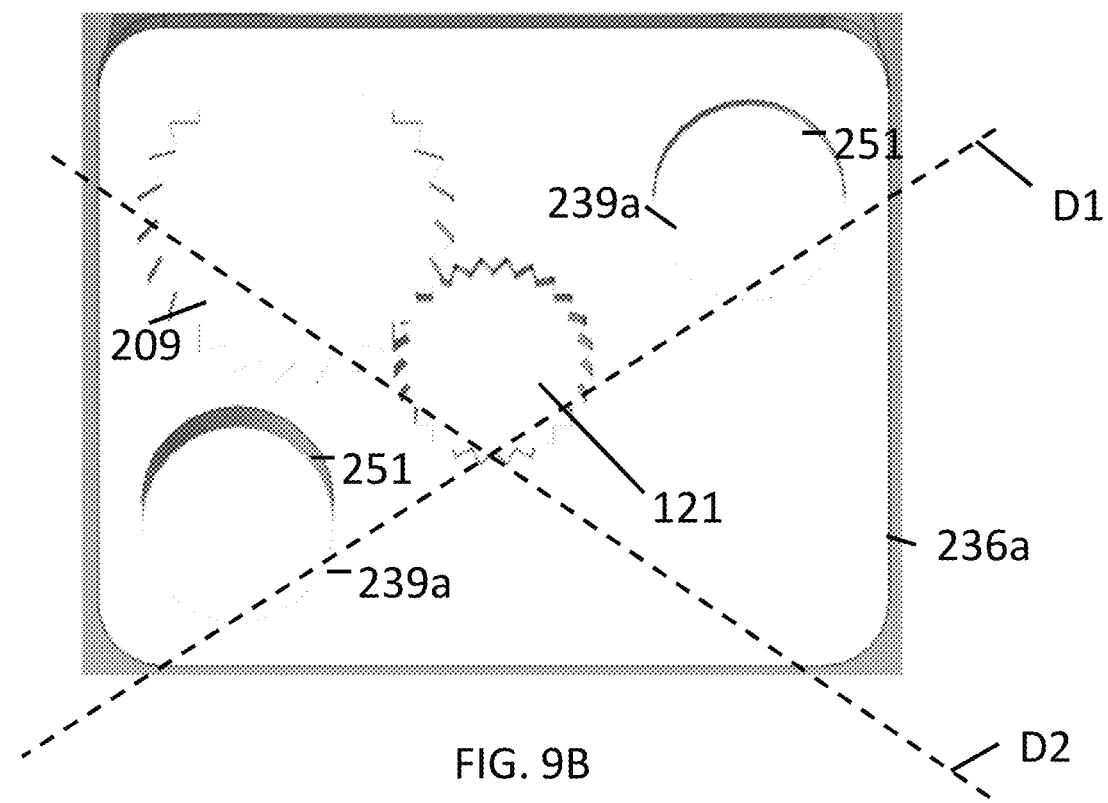
FIG. 9B is a cross-sectional view of the gear box assembly taken along line B-B of FIG. 7A spaced forwardly of line A-A and looking rearwardly at the first plate of the gear box assembly.
Figure 9C:
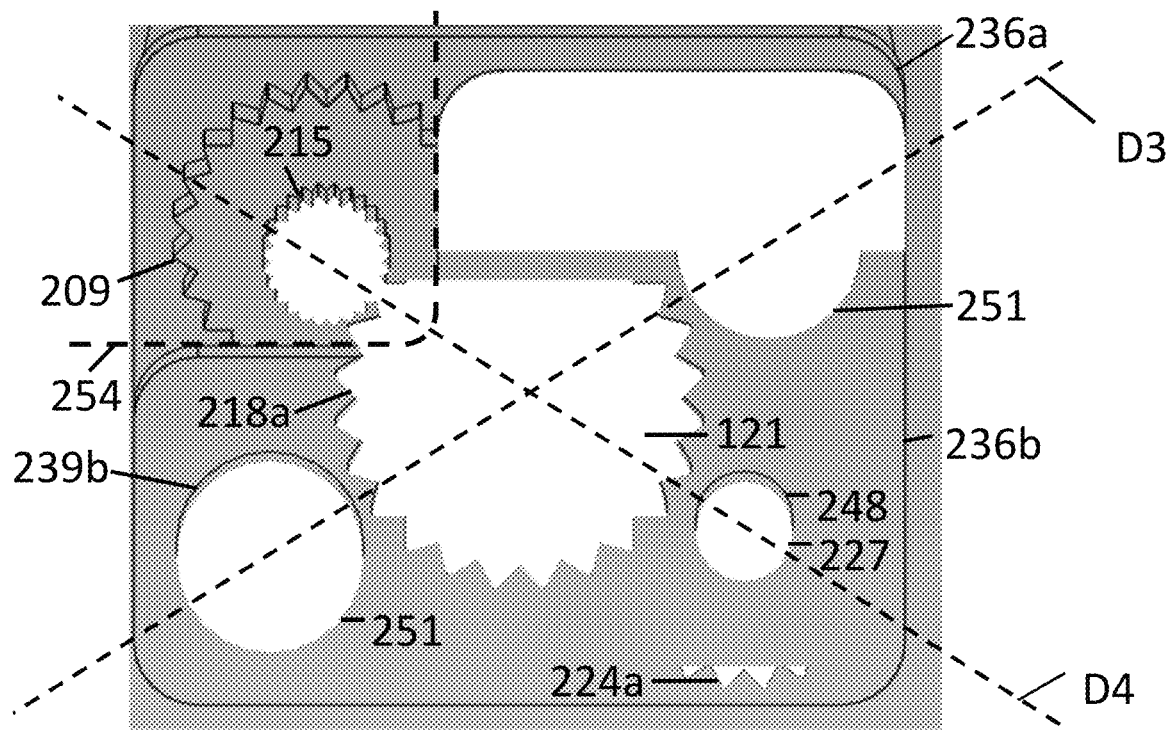
FIG. 9C is a cross-sectional view of the gear box assembly taken along line C-C of FIG. 7B looking rearwardly at a second plate of the gear box assembly.
Figure 9D:
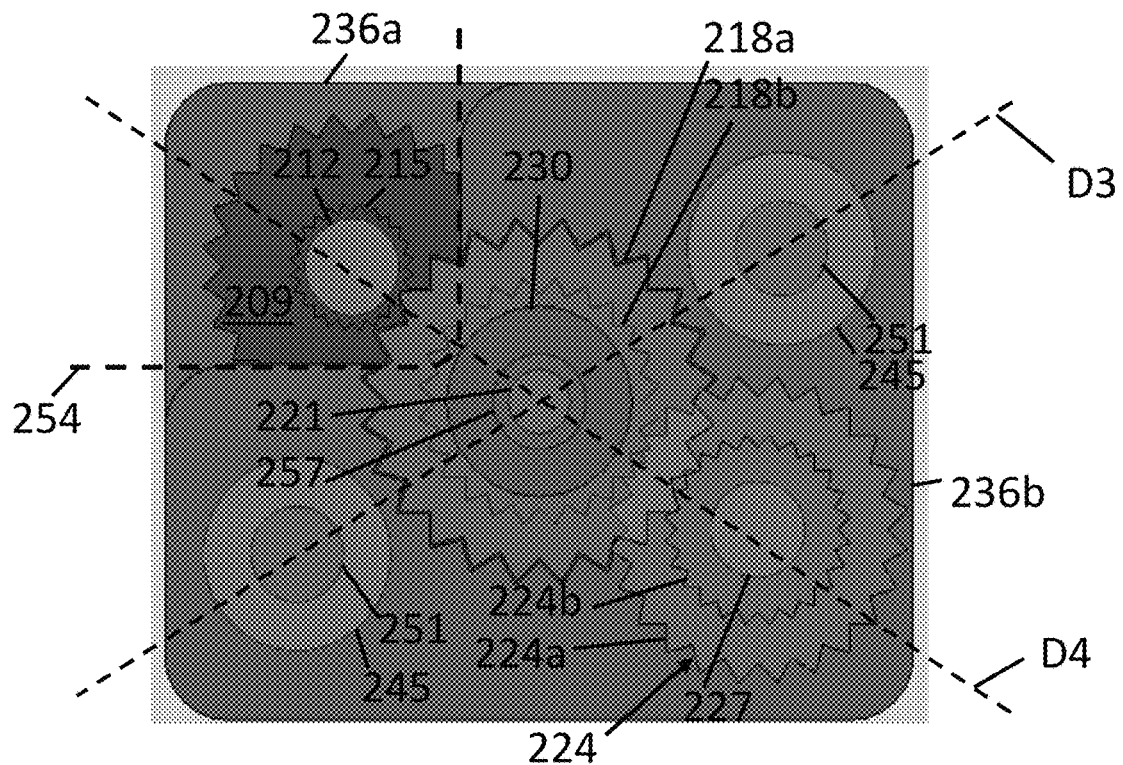
FIGS. 9D-E are a cross-sectional views of the gear box assembly taken along parallel, but axially spaced apart, planes D-D of FIG. 7A and E-E of FIG. 7B, respectively looking rearwardly at the second plate of the gear box assembly.
Figure 9E:
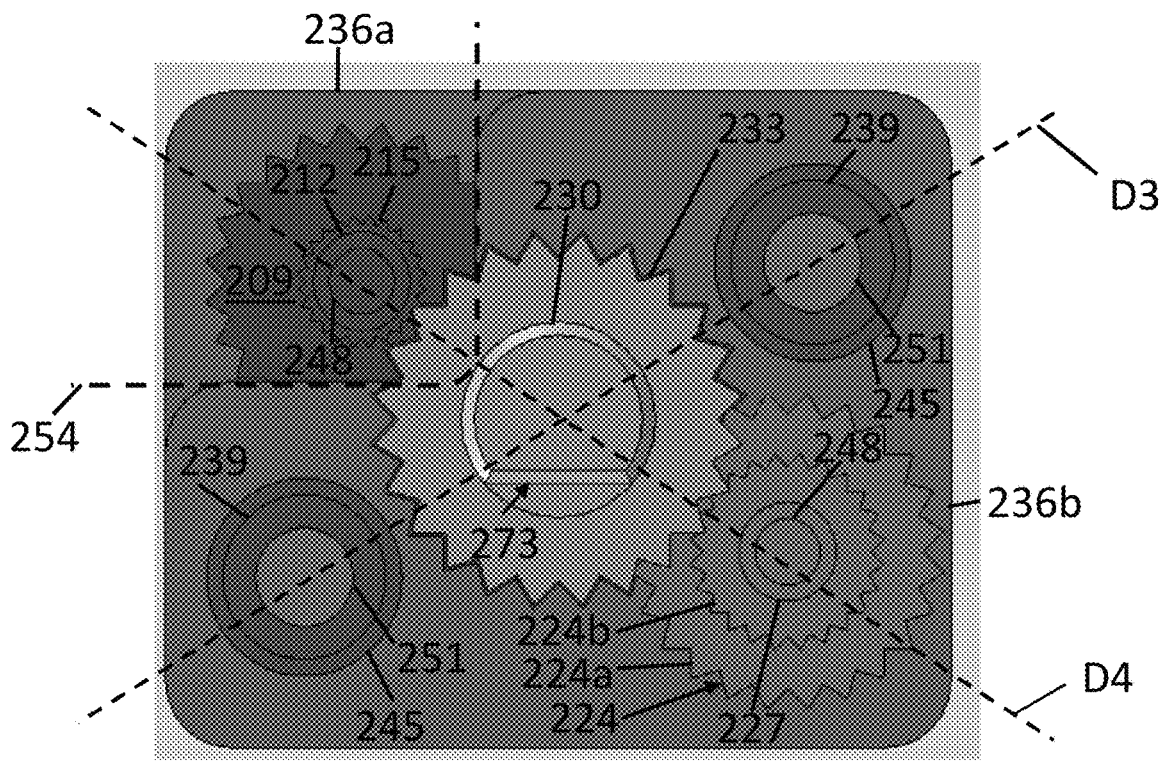
Figure 9F:
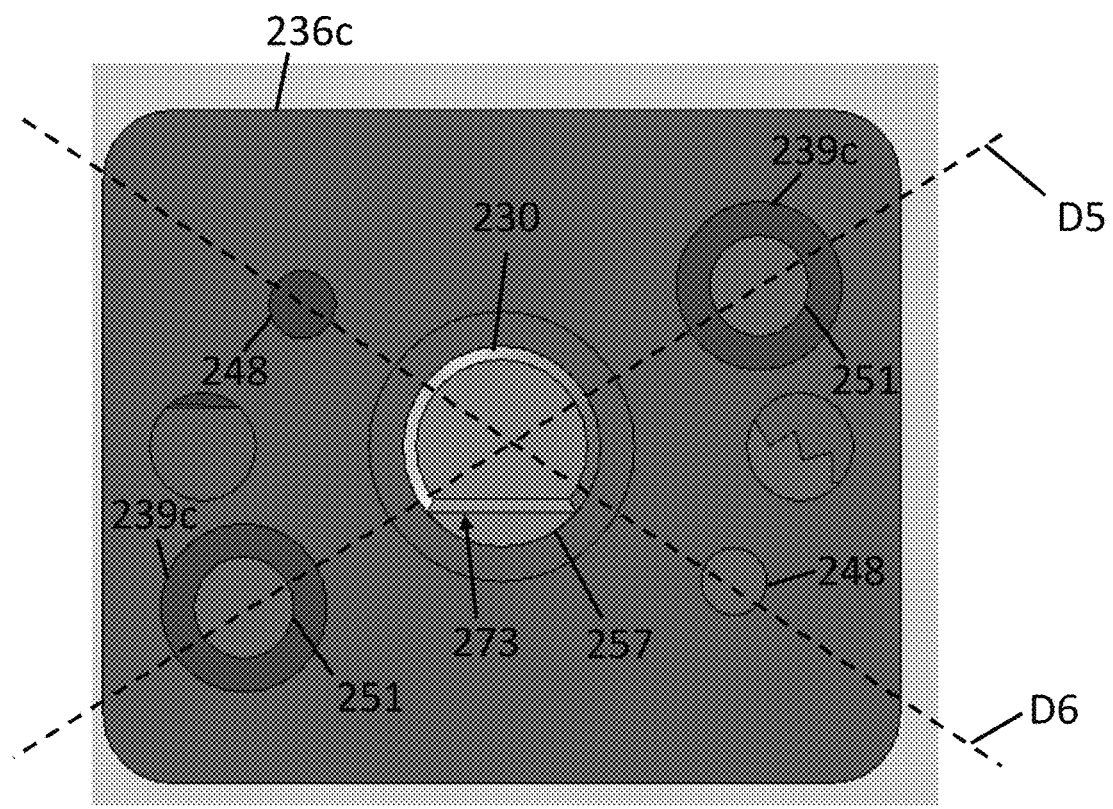
FIG. 9F is a cross-sectional view of the gear box assembly taken along line F-F of FIG. 7A looking rearwardly at a third plate of the gear box assembly.

The gear box assembly 203 has a boxlike configuration, such that all of the gears of the gear box assembly 203 fit into a predefined region. The motor 90 has a base facing end and a distal facing end. The gear box assembly 203 extends from the distal facing end of the motor. The gear box assembly 203 is partitioned into two distinct regions defined by three plates 236*a-c* which support the driven shafts 212, 221, and 227 and the output shaft 230, and which are supported by support posts 245, 251. The first plate 236*a* abuts the distal facing end of the motor 90, and can be fixed to the motor's end plate. The first plate 236*a* comprises two shaft holes 239*a* and one drive hole 242 fixed on a line D1 that runs diagonally through the center of the plate 236*a* connecting two of the corners. (FIG. 9A) The drive hole 242 falls on the center of the diagonal line D1 and is sized to receive the motor output shaft 118. The two support shafts thus on opposite sides of the drive hole 242. The motor output shaft 118 protrudes fully through the drive hole 242, such that the motor output gear 121 is adjacent a forward surface of the plate 236*a*. The two shaft holes 239*a* are sized to fit two support posts 245, one in each hole. The support posts 245 support the second plate 236*b* spaced from the first plate 236*a* to define the first distinct region. The first distinct region is large enough to allow the motor output gear 121 to rotate freely when the motor 90 is active. A second diagonal line D2 runs between the other two corners of the first plate 236*a* and intersects the first line D1 at the center of the first drive plate 236*a*. The drive hole 242 is defined at this intersecting point. A smaller first drive shaft hole 248 sized to accept the first driven shaft 212 is formed on the line D2 on a first side of the drive hole 242. As seen in FIG. 9A, an imaginary line running through the centers of hole 248 and one of the support post holes 239*a* is generally parallel to a side edge of the plate 236*a*. This hole 242 receives the first driven shaft 212 on which are mounted the first driven gear 209 and the pinion gear 215. The hole 248 is positioned at a distance from the drive hole 242 to allow the motor output gear 121 to mesh with the first driven gear 209.

Figure 7A:
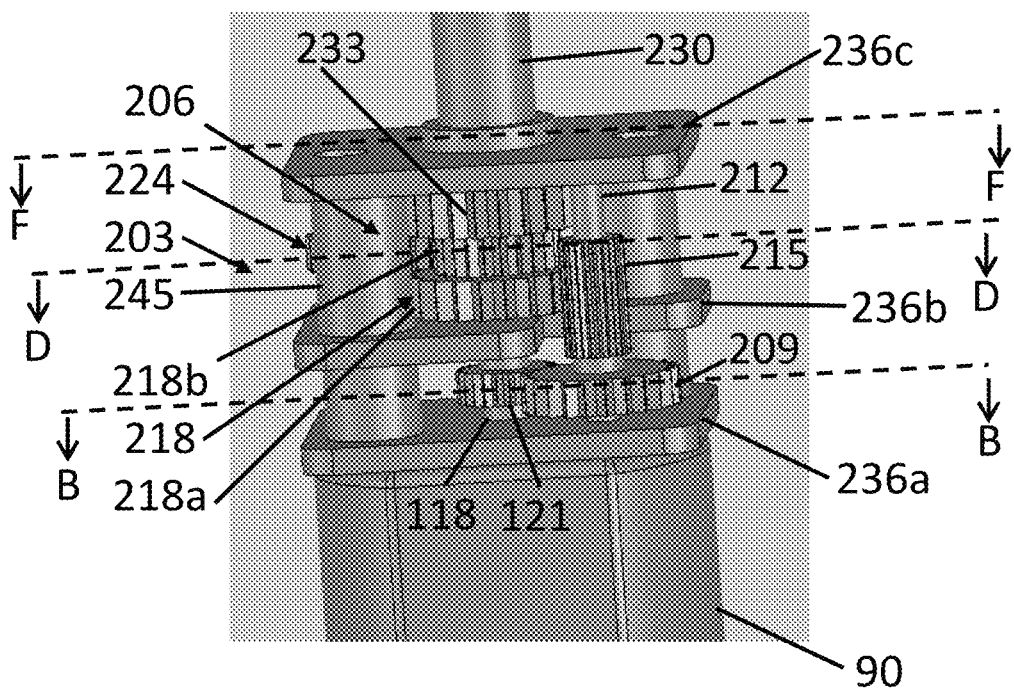
FIGS. 7A and 7B are fragmentary perspective views of a gear box assembly of the drive mechanism.
Figure 7B:
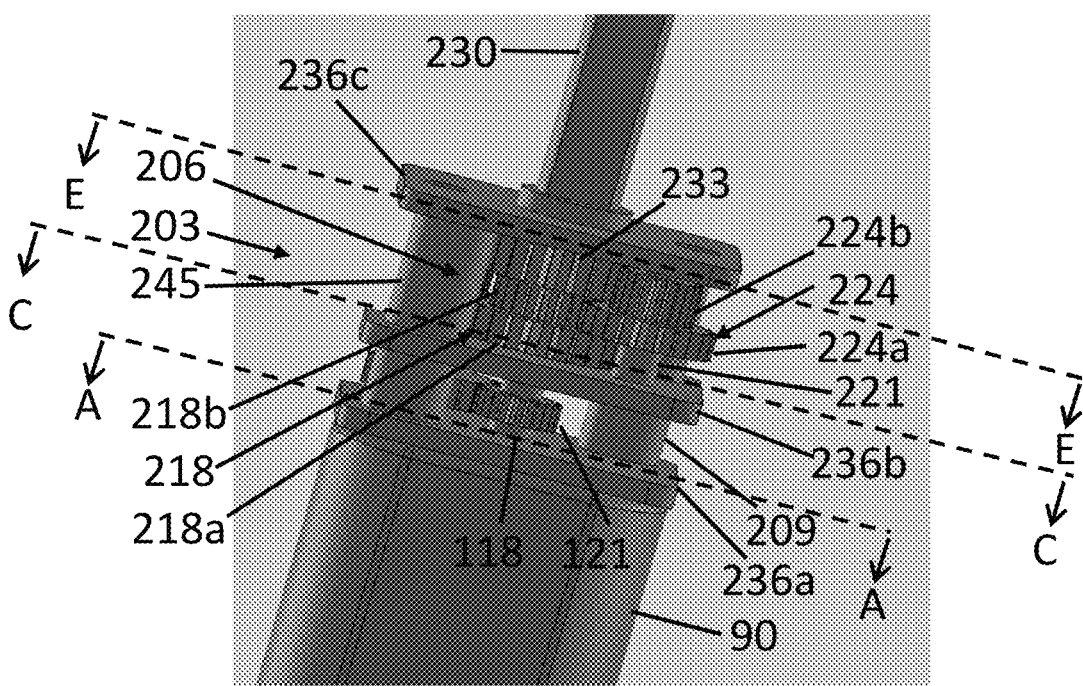

The second plate 236*b* is positioned parallel to the first plate 236*a* and is supported by the two supports 245. This second plate has two shaft holes 239*b* positioned on two axially extending lines L1, L2 (FIGS. 8B, C) that run perpendicularly to the plates 236*a*, 236*b* through the center of the shaft holes 239*a* on the first plate 236*a*. These holes 239*b* are sized to allow a support post 251 to pass through, allowing the supports 245 and the shaft holes 239*a* in the first plate 236*a* to receive the base end of the support shafts 251. If desired, the support posts 251 could be continuations of the support posts 245. The support post holes 239*b* on the second plate 236*b* rest on a line D3 (FIG. 9C) that is parallel to the first line D1. The second plate 236*b* defines a second diagonal line D4 that runs parallel to line D2. A notch 254 is cut out from the corner of the second plate 236*b* above the first driven gear 209 and pinion gear 215. The notch 254 defines an opening through which the pinion gear 215 extends, as seen in FIG. 7A, such that the pinion gear can extend into the second distinct region defined by the three plates 236*a-c*. Thus, when the motor output gear 121 rotates the first driven gear 209 in the first distinct region, the pinion gear is rotating in the second distinct region. At the point where diagonal lines D3 and D4 intersect, a drive shaft hole is defined to receive the base end of the second driven shaft 221. A hole is defined at the center of the first gear set 218, sized to allow the base end of second driven shaft 221 to fully pass through prior to being received by the drive shaft hole 248. In the variation where the second driven shaft 221 and the output shaft 230 are a unitary shaft, the first gear set 218 is allowed to freely rotate around base end of the driven output shaft 230 in the distinct second region defined by the drive box plates 236. The driven portion 218*a* of the first gear set 218 is sized to mesh with the pinion gear 215 as it passes through the notch 254 in the second drive box plate 236*b*. Near the corner on the second drive box plate 236*b* that lies on line D4 opposite the notch 254, a second drive shaft hole 248 is defined. This hole receives the base end of the third driven shaft 227. The third driven shaft 227 extends towards the distal end of the handpiece 10 away from the second drive box plate 236*b* when mounted. The second gear set 224 is defined with a hole in the center through which the third driven shaft 227 passes prior to being secured at the base end to the second drive box plate 236*b*. The center hole on the second gear set 224 is sized to receive the third driven shaft 227 while also being free to rotate.

The driven output gear 233 is positioned near the distal end of the first gear set 218. The center axis of the driven output shaft 230 is secured at the base end to the second drive box plate 236*b*. The first gear set 218, the driven output gear 233, and the driven output shaft stack in this order as the shaft extends towards the distal end of the handpiece 10.

The third plate 236*c* (FIG. 9F) is positioned parallel to the first and second plates 236*a*, 236*b* and is supported by the support posts 251. It is positioned to accept and secure the distal end of the first driven shaft 212 and the third driven shaft 227. A fifth diagonal line D5 that is parallel to both line D1 and line D3 runs between two corners of the plate 236*c*. Positioned on this line are two support shaft holes 239*c* and a driven output shaft hole 257. The two support shaft holes 239*c* are concentrically and collinearly aligned with the support shaft holes 239*a,b* of the plates 236*a,b*, so that lines L1 and L2 run through the centers of the two support shaft holes 239*c*, respectively. A sixth diagonal line D6 runs along the third drive box plate 236*c* parallel to both D2 and D4. Lines D5 and D6 intersect at a point in the center of the third drive box plate 236*c*. The driven output shaft hole 257 is centered on this intersecting point. The driven output shaft hole 257 is sized to receive and allow the driven output shaft 230 to pass through, so as to extend towards the distal end of the handpiece 10. Two drive shaft holes 248 are positioned on line D6 for accepting and securing the distal ends of the first driven shaft 212 and the third driven shaft 227. The holes are positioned so that the first driven shaft 212 and the third driven shaft 227 extend perpendicularly between the second drive box plate 236*b* and the third drive box plate 236*c*.

The driven output shaft 230 extends from the third plate 236*c* of the gear box 203 towards the head of the handpiece 10 and includes an output shaft gear member 276 fixed to the distal end thereof which rotates with the output shaft 230. The driven output shaft has a flat keying surface 273 at its distal end extending parallel to the axis 285 of the output shaft 230. The center axis 285 of the output shaft gear member 276 is coaxial with the output shaft 230, such that the gear member 276 rotates about the center axis 285.

Figure 10A:
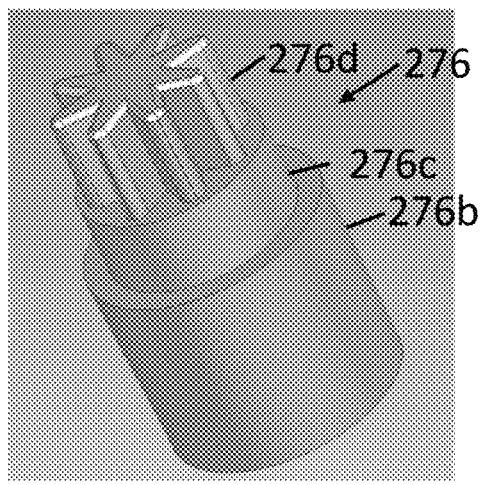
FIGS. 10A-B are perspective and bottom plan views of a gear member mounted at the end of an output shaft of the drive mechanism.
Figure 10B:
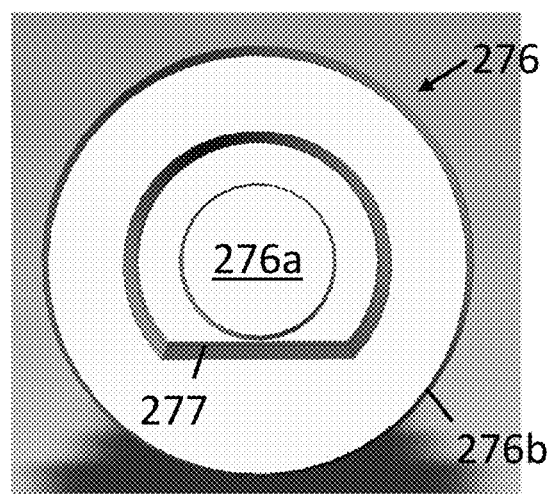

As shown in FIGS. 10A-C, the output shaft gear member 276 comprises a base portion 276*b*, a central portion 276*c* and a distal gear portion 276*d*. The base portion 276*b* defines a base end cavity 276*a* (FIG. 10B) which receives the driven output shaft 230. This cavity 276*a* is shaped correspondingly to the distal end of the output shaft 230, such that the gear member 276 will be rotationally fixed to the output shaft 230. To this end, the cavity 276*a* has a flat wall 277 which engages the flat surface 273 of the output shaft 230 to rotationally fix the output shaft gear member 276 relative to the output shaft 230. The central portion 276*c* of the gear member is positioned between the distal end of the base portion 276*b* and the base end of the distal gear portion 276*d*. The radius of the central portion 276*c* is smaller than the radius of the base portion 276*b*, and thus defines a step. The central portion 276*c* has a generally smooth exterior.

Figure 13A:
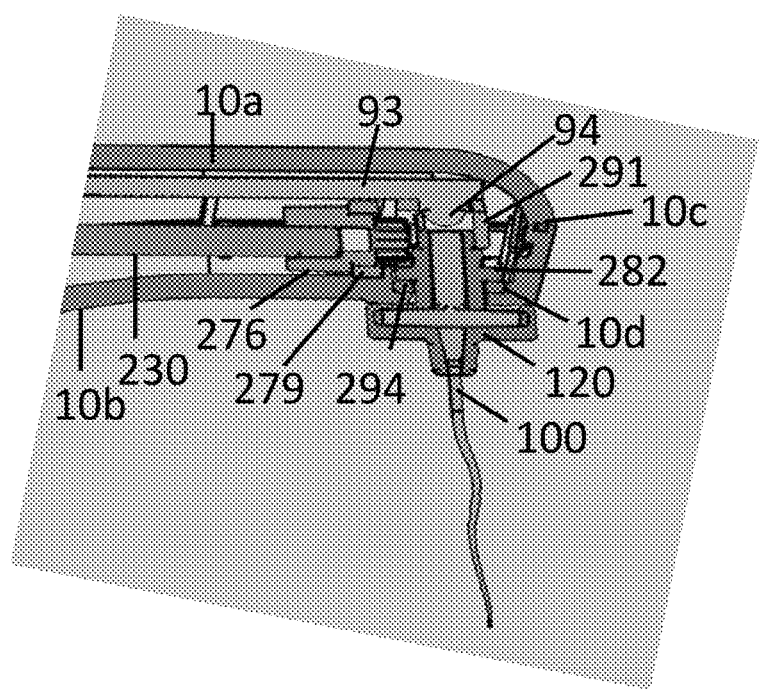
FIG. 13A is a fragmentary cross-sectional view of a portion of the drive mechanism in the head of the handpiece with a light guide received in the light guide receiving gear member.
Figure 13B:
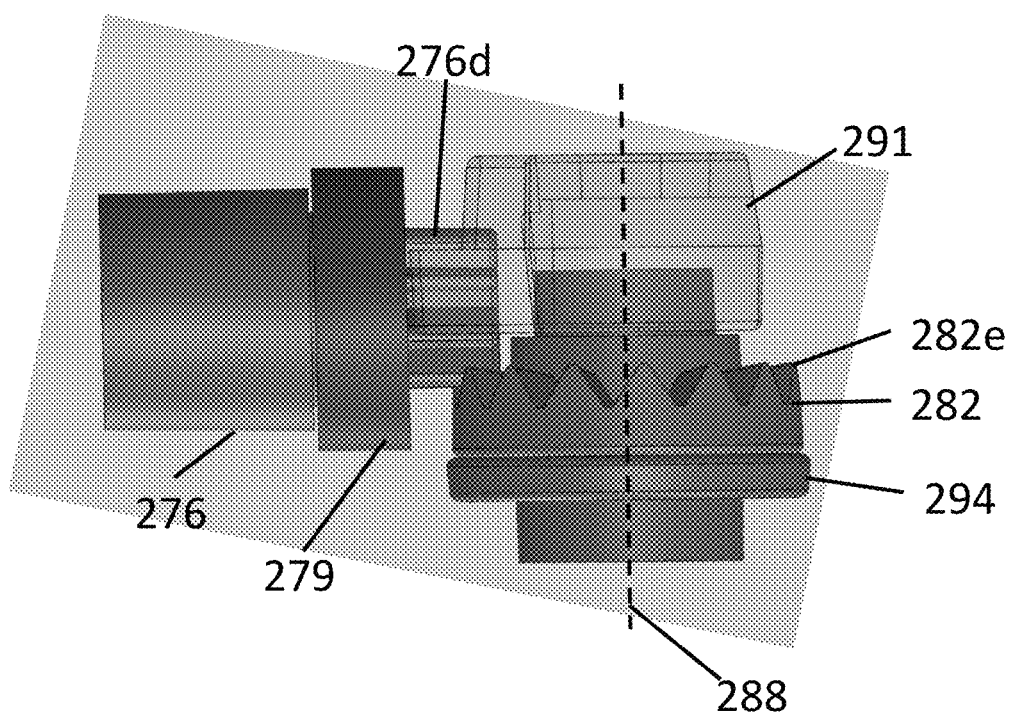
FIG. 13B is an elevational view showing the interconnection of the output shaft gear member and the light guide receiving gear member with the gear sleeve cover shown in phantom.

A driving axis bracket 279 (FIGS. 13A, B) is positioned about the central portion 276*c* of the output shaft gear. The driving axis bracket 279 is shaped as a ring that encircles the central portion 276*c* of the gear member 276. As seen in FIGS. 13A and 13B, the driving axis bracket 279 is positioned in the handpiece housing between a bottom surface of the housing and the light PCB 93, and thus operates as a journal bearing which helps fix the relative position of the output shaft gear member 276 in the head of the handpiece. The driving axis bracket 279 is sized (i.e., has a front-to-back width) such that the distal gear portion 276*d* will protrude beyond the distal surface of the driving axis bracket 279.

A light guide receiving gear member 282 (FIG. 11) is positioned in the head 13*d* of the handpiece to rotate about an axis which intersects the axis of the output shaft gear member 276. Preferably the light guide receiving gear member 282 is generally perpendicular to the output shaft gear member 276. The two gear members could define other angles, if desired. The light guide receiving gear member 282 (FIG. 11) comprises a hollow central sleeve 282*c* and an annular flange 282*a* which extends from the approximate center of the sleeve. Teeth 282*e* on the annular flange 282*a* form a gear on an upper surface of the flange 282*a*. The sleeve extends both above and below the flange to define a top portion 282*b* and a bottom portion 282*d* of the sleeve. The top portion 282*b* extends towards the top cover 10*a* of the handpiece 10 from the gear portion 282*a*. The top portion 282*b* of the gear sleeve 282 is stepped, to define a portion 282*f* of reduced diameter. The sleeve 282*c* defines a passage 282*g* which, as described below, will receive a stem of a light guide, and through which light from the light source 94 will pass. As shown in the drawings, the light source 94 is positioned on an axis of the light guide holder to direct light directly to the light guide. However, handpiece could be configured in different ways such that the light from the light source is directed to the stem of the light guide. For example, the handpiece could be provided with a light tube (i.e., a fiber optic) which directs light from the light source to the stem of the light guide, thereby allowing the light source to be positioned in any desired location in the handpiece. In addition, the light guide holder could be made of light transparent material, and the light could pass through the sleeve of the light guide holder into the light guide. In this example, the light can be directed at the sleeve of the light guide holder from most any angle.

The gear members 276 and 282 are positioned in the head so that their respective teeth mesh, such that the output shaft gear member 276 will drive the light guide receiving gear member 282. A gear sleeve cover 291 (FIGS. 12A-D) is positioned in the head of the handpiece. The gear sleeve cover, in part, serves to maintain the positions of the gear members 276 and 282 relative to each other so that they will mesh, and thus transition the horizontal rotational/reciprocal motion of the output shaft to vertical rotational/reciprocal motion.

The gear sleeve cover 291 comprises a base portion 291a, an upper portion 291b, a top surface 291g that faces the top shell 10a, and a bottom surface 291h that faces the bottom shell 10b of the handpiece 10. A cylindrical through passage 291c sized to receive the reduced diameter portion 282f of the light guide receiving gear member 282 extends between the top surface and the bottom surface. The passage 291c is generally cylindrical in shape with the center positioned to extend parallel to the axis 288 of the light guide receiving gear member 282.

Figure 12C:
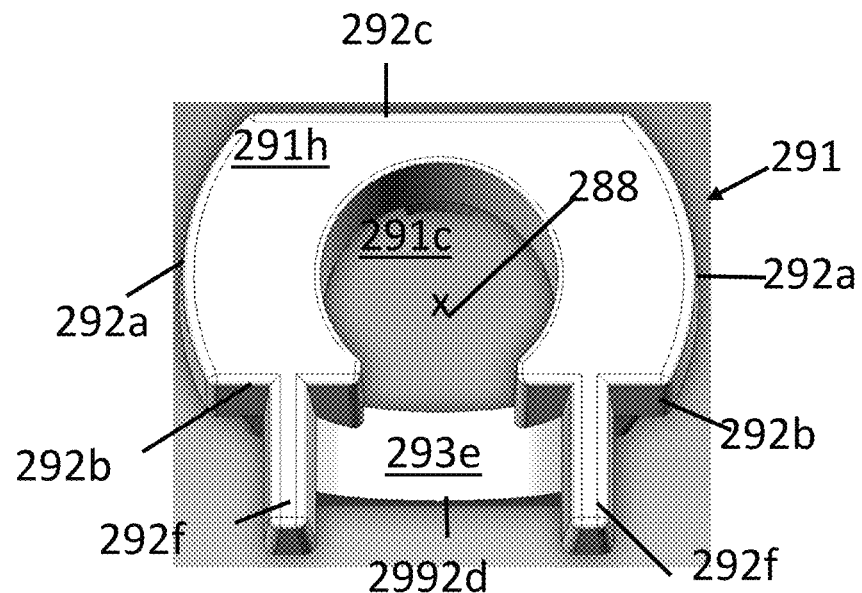

As best seen in FIG. 12C, the base portion 291a is generally in the shape of a flattened omega (Ω) or a flattened horseshoe. To this end, the base portion of the gear sleeve cover comprises opposed arced side portions 292a which have flat end surfaces 292b extending between the distal ends of the side portions. The wall 292c joining the side portions is flat. The outer surface of the side portions 292a are arced and define a radius. A pair of spaced apart arms 292f which extend rearwardly from the flat distal surfaces 292b of the side portions. As seen, the arms 292f extend generally from a midpoint of the flat end surfaces 292b. The space 292d between the side portions defines an opening into the passage 291c. The space 292d is sized to permit passage of the geared portion 276d of the output shaft gear member 276. The portion of the flat end surface 292b between the arms 292f and the opening 292d define a stop to prevent the gear member 276 from extending too far into the central opining 291c.

The upper portion 291b of the gear sleeve cover continues the flattened omega shape of the base portion. The upper portion comprises opposed arced side walls 293a, the exterior of which define a radius, and which have flat end surfaces 293c. A side wall 293d extends rearwardly from each of the end surface surfaces 293c of the upper portion 291b. The side walls 293d are connected by an arched surface 293e and by the top surface 291g, effectively forming an arched passage leading into the entrance 292d to the passage 291c of the gear sleeve cover. The side walls 293d of the top portion, as seen best in FIG. 12A, are atop the arms 291f of the base portion and are shorter than the arms 291f of the base portion. Thus, the arms 291f protrude from beneath the walls 293d.

Figure 12D:
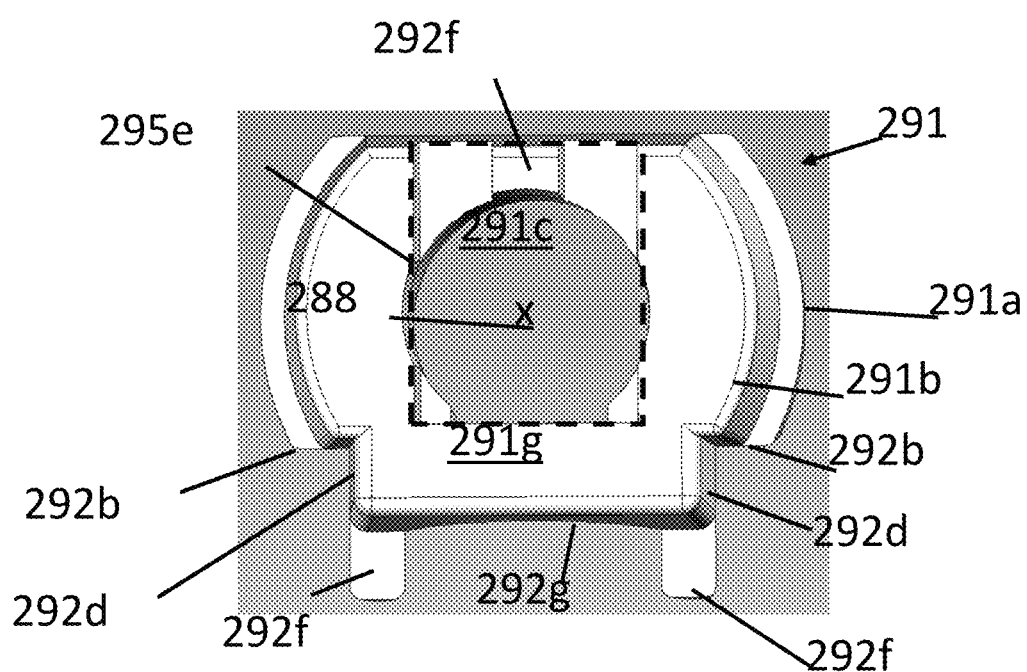

Lastly, a cutout 295e, defined by a dashed rectangular region in FIG. 12D, extends rearwardly from the flat distal surface of the top portion 291b to a point approximately even with the end surface 293c of the arced wall 293a of the top portion 291b. This cutout is open to the top surface, and thus defines a generally rectangular cavity that opens towards the distal end of the top portion. A positioning tooth 292f extends upwardly between the opposite sides of the cutout at the distal end of the top portion, as shown in FIGS. 12A and 12D.

The gear sleeve cover 291 can also be seen as being in the shape of a flattened igloo. The igloo comprises a main body comprised of the base and upper portion (291a, b and an arched doorway, defined by the arms and walls 292e, 293df, and 292gd. The upper and lower portions thus define a stacked cylinder configuration, with the bottom cylinder having a larger radius than the top cylinder. The center axis 288 of the cover 291, best shown in FIG. 12B as a dashed line, and FIGS. 12C and 12D as an 'x', defines the center axis of a cylindrical passage 291c extending between the top surface 291g of the upper portion 291b and the bottom surface 291h of the bottom portion 291a. The stacked cylinder configuration of the main body comprises the flat end surfaces 292b at the front which lies in a plane parallel to the axis 288. The space between the flat end surfaces 292b define the entryway 292d to the passage.

An arched doorway of the flattened igloo shape extends generally perpendicularly away from the flat surface 292b. The arched doorway is defined by the side members 292f, 293c, top surface 291g, and front surface 292g to create a tunnel-like entrance. The archway or tunnel-like entrance 291e defines an entrance passage to the entryway 291d which leads into the cylindrical passage 291c.

Figure 5A:
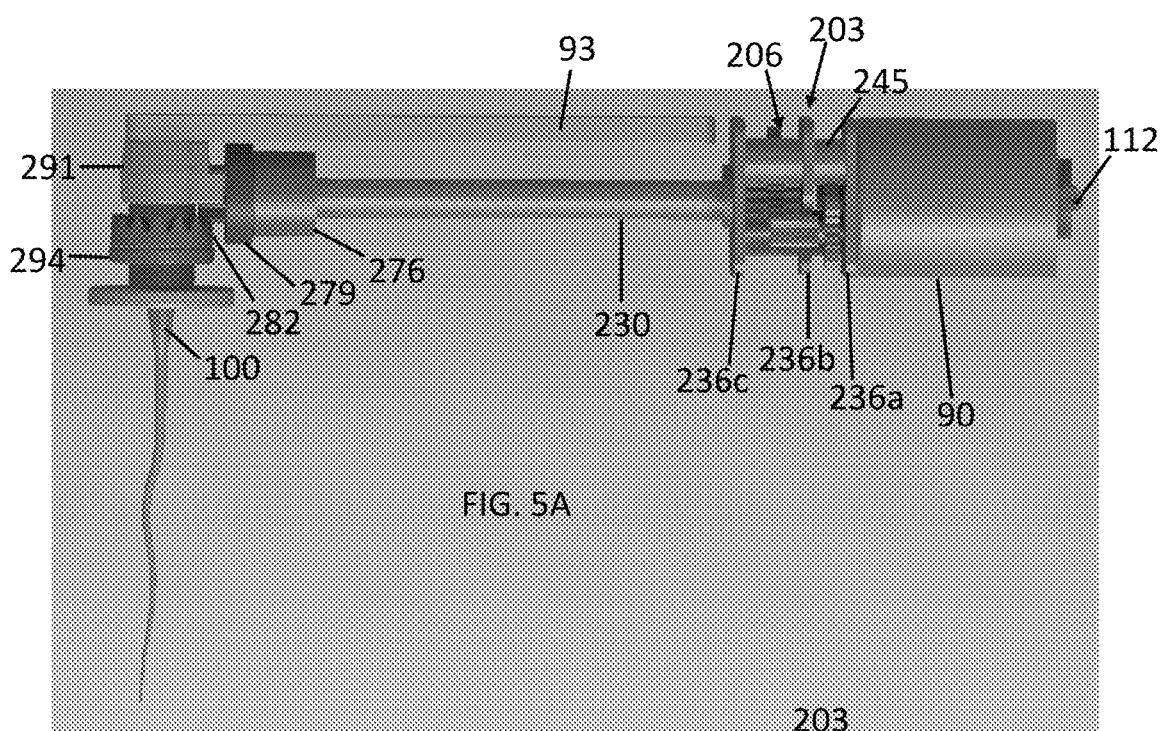
FIG. 5A is a side view of a drive mechanism and light source of the handpiece with a light guide.
Figure 5B:
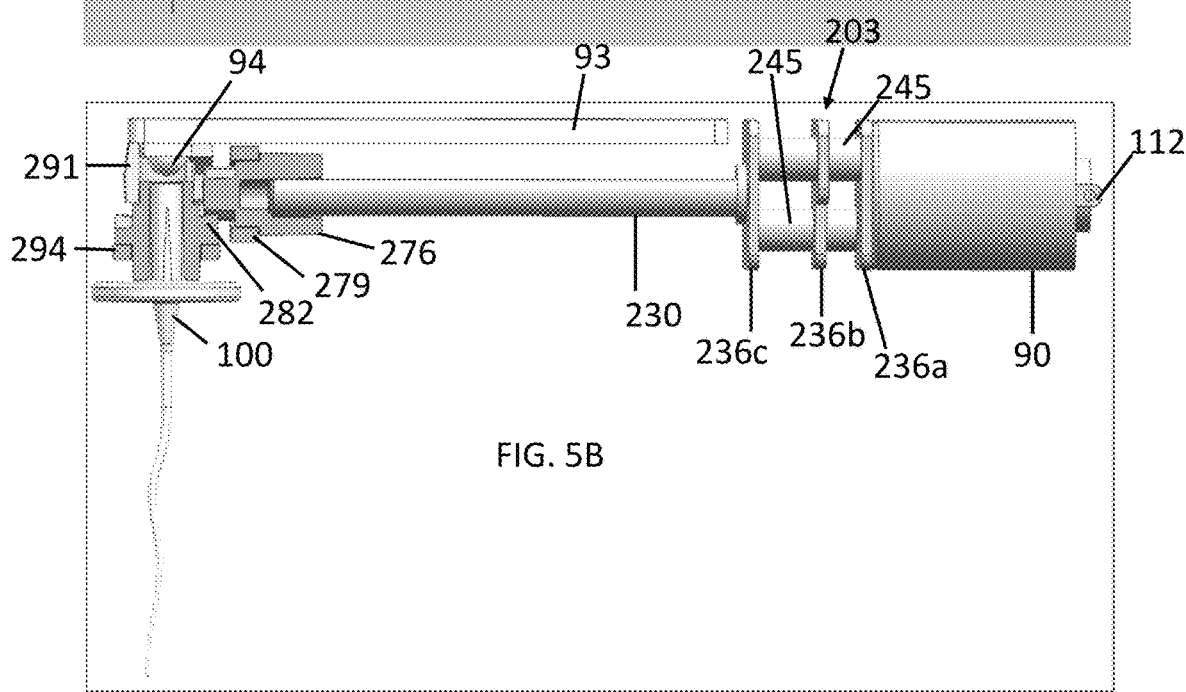
FIG. 5B is a partial cross-sectional view of the drive mechanism and light source with a light guide.
Figure 6A:
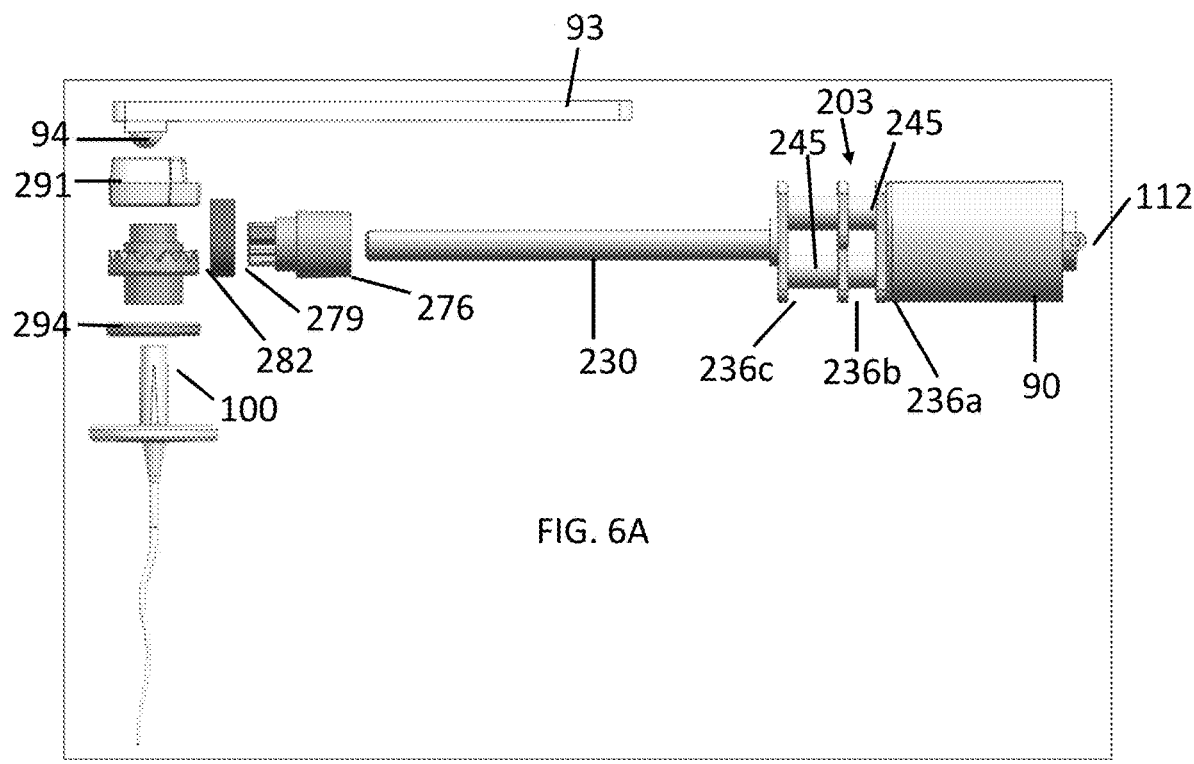
FIGS. 6A and 6B are exploded elevational and perspective views, respectively, of the drive mechanism of the handpiece with the light source and a light guide.
Figure 6B:
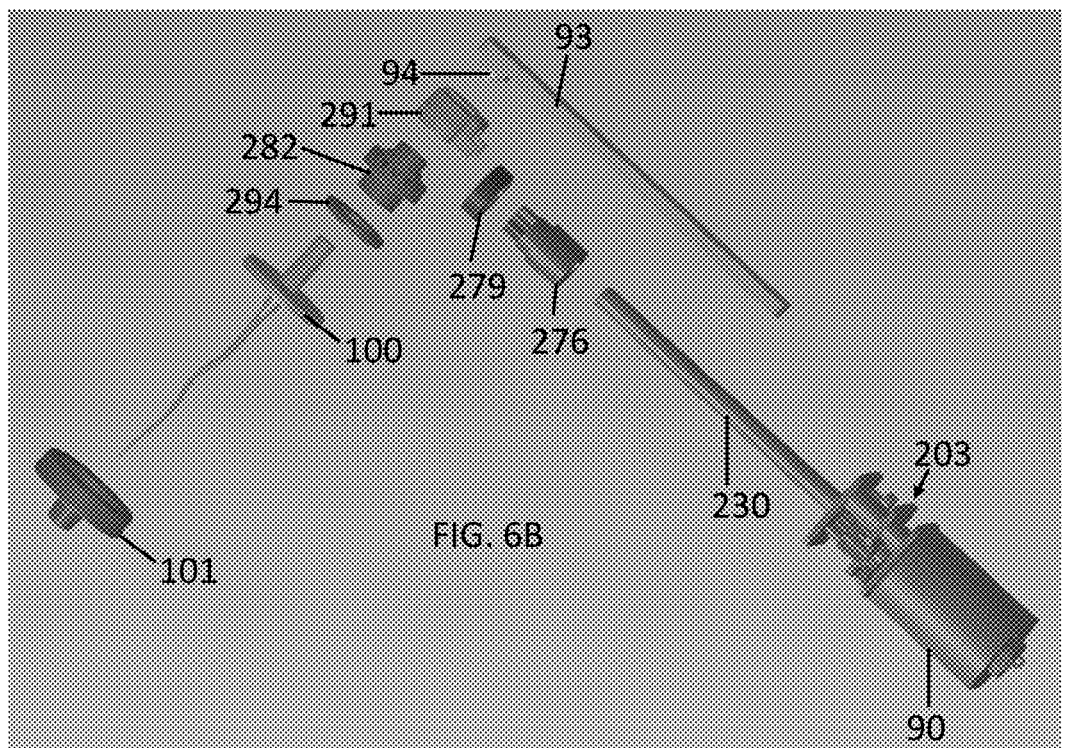

The gear sleeve cover and light board 93 are positioned such that the passage 291c is aligned with the light source 94. Further, as seen in FIGS. 5B and 13A, the passage 291c is sized to receive the light source 94, such that light from the light source 94 will shine through into passage 291c from the top surface 291g of the cover in a direction towards the bottom surface 291h of the main body portion 291a.

Figure 13C:
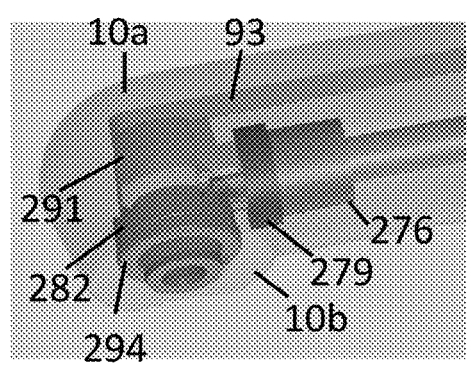
FIGS. 13C and 13D are fragmentary perspective views of the portion of the drive mechanism in the head of the handpiece with the housing of the handpiece shown in phantom.
Figure 13D:
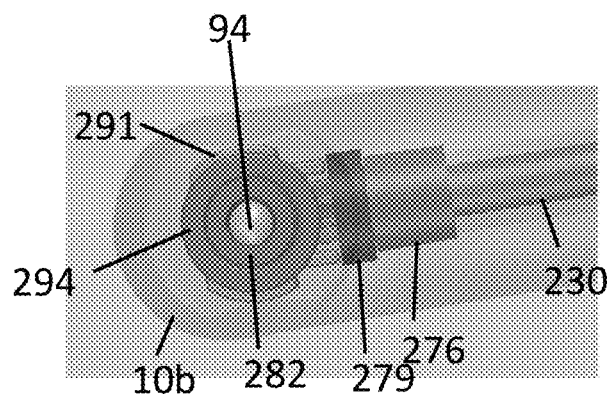

The passage 291c is sized to receive the top portion 282b of the light guide receiving gear member 282. In the fully received position, the top portion 282b of the light guide gear member 282 extends into the base portion 291a from the bottom of the cover, but does not extend into the upper portion 291b of the gear sleeve cover (which is occupied, in part, by the light source 94). The radial surface defined by the step in upper portion 282b of the sleeve 282c of the light guide receiving gear member acts as stop to prevent further insertion into the passage 291c of the cover. As seen in FIG. 13D, the teeth 282e on the flange 282a of the gear member 282 define a circle, the circumference of which is positioned under the arms 291f extending from the base portion 291a of the gear sleeve cover 291, such that the teeth 282e of the gear member 282 face upwardly towards the bottom surface 291h.

The entryway 291d of the gear sleeve cover is sized to receive the gear portion 276d of the output shaft gear member 276. The gear portion 276d of the output shaft gear member 276 extends between the arms 291f of the base portion 291a. As seen in FIGS. 13B-D, the annular ring bracket 279 is adjacent the distal surface of the arms 291f on the central portion 276c driving axis gear member to prevent the gear portion 276d from entering the passage 291c, such that the gear portion 276d will mesh with the teeth 282e of the gear member 282.

When the handpiece 10 is assembled with the top shell 10a and the bottom shell 10b pressed together, the gear sleeve cover 291 provides component alignment support for the head gear assembly (i.e., the gear members 276 and 282). The alignment of the base portion 291a and the upper portion 291b with the central axis 285 and the perpendicular axis 288 secure the driving components into place. Starting from the top end, the light source 94 is received in the top of the passage 291c of the gear sleeve cover 291. The top portion 282b of the light guide receiving gear member, as noted, is received in the passage 291c through the bottom surface 291h of gear sleeve cover 291. When the light guide receiving gear member 282 is fitted into the gear sleeve cover 291, the teeth 282a of the gear sleeve 282 rests below the bottom surface of the gear sleeve cover 291, meshing with the distal gear 276d of the output shaft gear member 276, such that the motion of the output shaft gear member will be transferred to the light guide receiving gear member. Additionally, the light source 94 is aligned with the passage 282g of the light guide receiving gear member such that the light from the light source will be directed through the passage 282g. As with the gears of the gear box assembly, the gear members 276 and 282 can be made of a plastic or from metal.

The bottom shell 10b defines inner surfaces which axially position the gear member 282 within the handpiece head to align with the opening 14 in the bottom surface of the handpiece head. A gear ring 294 is positioned about the bottom portion 282c of the gear sleeve 282 below the bottom surface of the flange 282a. As seen, for example in FIG. 13A, the gear ring 294 is positioned in a seat 10d in the housing bottom shell 10b between the flange portion 282a and the bottom surface of the head. When the handpiece 10 is fully assembled, the gear ring 294 provides a low friction surface to facilitate rotation of the gear member 282 within the head. The gear member 282 is thus securely fit into the assembled handpiece 10 so that it is free to rotate when the motor 90 is activated but is secured and protected from additional vibrations that may otherwise cause damage.

The gear sleeve cover 291 is described as an individual component, which is positioned in the top shell 10a, b of the housing 13. However, the top and bottom shells 10a, b of the housing could be formed (molded) to define the surfaces which receive the gear members 276 and 282 and bring them into meshing contact with each other. Further, such molding could align the light source 94 with the passage 291c, such that the light from the light source 94 shines down, into the passage 291c. Housing shells configured in this manner would obviate the need for a separate cover 291.

A series of light guides 100A-1001 are shown in FIGS. 14A-23C. Each light guide comprises a circular disc-shaped base plate 104, a stem 102 extending upwardly from the base plate 104 and a respective probe 106A-1 extending downwardly from the base plate 104. The base plate 104 is generally disc-shaped with a radius approximately equal to the radius of the bottom head surface. As such, the base plate portion 104 serves as a shield to reduce the potential for fluids, bacteria, etc. from splashing up into the head through the opening 14. The stem 102 is sized to be frictionally received in the cylindrical passage 282g of the light guide receiving gear member. When received in the handpiece head, the disc 104 will be adjacent the bottom of the handpiece head. The stem 102 of each light guide is generally cylindrical, but tapers slightly from the base 104 upwardly. A plurality of fins 106 extend upwardly from the base 102 and are spaced (preferably equiangularly) about the exterior surface of the stem. The fins increase the radius of the stem sufficiently to form a frictional fit of the stem within the gear member sleeve to positionally secure the light guide to the gear member 282. Thus, when fully inserted into the passage 282d within the gear member 282, the light guide will be securely positioned with the head gear assembly to be rotationally driven when the motor is activated. As seen in FIGS. 15B and 16B, when the light guide is received in the handpiece head, the stem passes through the head opening 14 into the cylindrical passage 282d of the gear member 282, and the base 104 of the light guide is below the bottom surface of the handpiece head.

Each light guide 100A-I has an associated shield or cover 120A-I that is affixed to the disc 103 of the respective light guide. The cover 120A-I provides additional protection and shielding to the light guide 100A-I, the opening 14 in the head of the handpiece, and the internal driving gear assembly when the handpiece 10 is in use. The cover 120A-I is opaque, and thus substantially prevents light from the light source from exiting the base 104 of the light guide, such that all light passes through the tip of the light guide. Each light guide cover 120A-I includes an attachment portion 122 sized to enclose the periphery of the base 104 of the light guide 100A-1. The attachment portion 101a is generally puck-shaped with a bottom surface 122a and a circumferential side wall 122b extending upwardly from the bottom surface, which in combination define cavity which is receives the base 104 of the light guides 100A-1 in a secure fit such that the cover 120A-I will rotate with the light guide 100A-1 if used with the motor is activated. The cover 120A-I is preferably made from a flexible/pliable material, so that the attachment portion 122B of the cover 122 can be fitted about the base 104 of the light guide 100A-I. A hollow nose 130A-I, particular for each light guide, extends from the attachment portion 122, and the probe 106A-1 extends, at least in part, through the nose 130A-I.

The light guides are made from a light transmissive (and preferably light transparent) material. Although, if desired, the base 104 need not be made from a light transmissive material (so long as there is a continuous light path from the top of the stem 102 to the top of the probe 106A-1. As best seen in FIGS. 5B and 13A, when the light guide 100A-1 is received in the light guide receiving gear member 282, the stem 102 of the light guide is axially aligned with the light source 94. The light source 94, when activated, will thus direct its light into the passage 291C of the cover 291 to enter the stem 102 of the light guide at the top of the stem. The light guide, as noted, defines a continuous light path from the top of the stem to the probe 106A-1. Thus, the light will travel down the stem 102 into the probe 106A-I to exit the probe 106A-I through either or both of the bottom and sides of the probe.

Figure 14A:
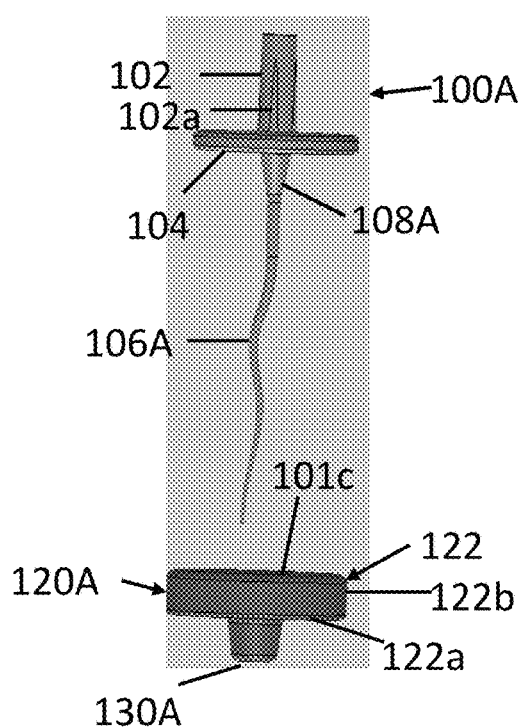
FIG. 14A is an exploded elevational view of a first light guide and an associated cover.
Figure 14B:
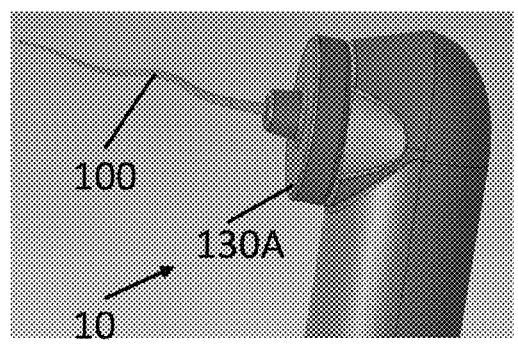
FIGS. 14B and 14C are fragmentary side elevational and cross-sectional views of the head of the handpiece with the first light guide.
Figure 14C:
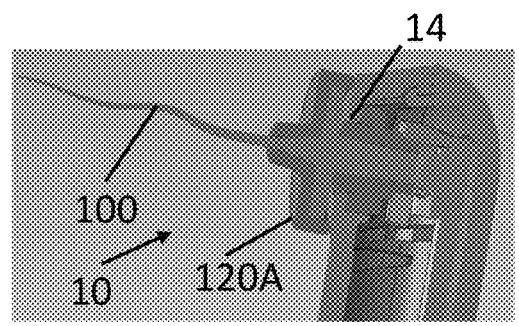

A first light guide 100A is shown in FIGS. 14A-C. The probe 106A of the light guide 100A is designed to extend substantially to the apical end of a root canal. The light guide 100A includes a short connecting section 108A which transitions between the probe 106A and the base 104. The nose 130A of the cover 120A is sized to encase this connection section, and the probe 106A extends from the end of the nose. Thus, light will exit the probe 106 through the sides and bottom of the probe. The probe 106A can be used to mechanically or dynamically activate fluid in a root canal (or other treatment area). As such, it is an "active" probe which is rotationally or reciprocally driven by the drive mechanism of the handpiece. Additionally, the light guide 100A can be used to transilluminate a tooth from within the root canal when the canal is free of liquid. This will facilitate in the visualization of cracks in the root of the tooth. When used to transilluminate a tooth, the light guide 100A will be used as a static probe (i.e., non-rotating), and thus will be used without engaging the motor. The probe 106A is made in accordance with the tip shown and described in US Pub. No. 2019/0290397 which is incorporated herein by reference, and has an S or spiral shape.

Figure 15A:
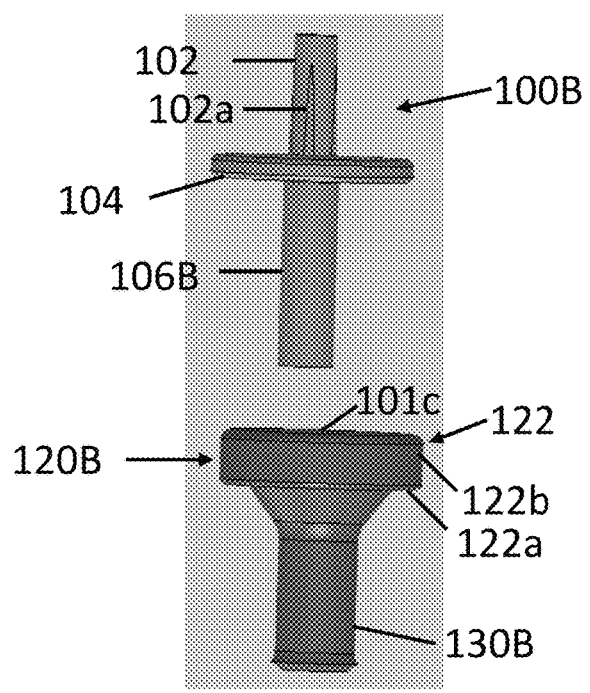
FIG. 15A is an exploded elevational view of a second light guide and an associated cover.
Figure 15B:
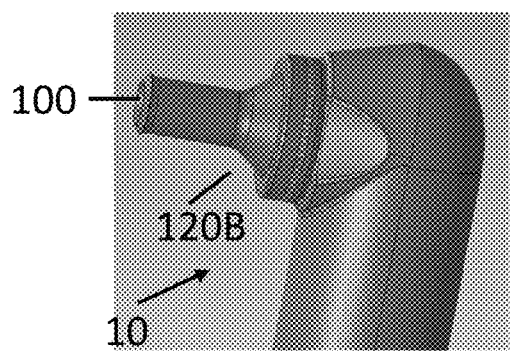
FIGS. 15B and 15C are fragmentary side elevational and cross-sectional views of the head of the handpiece with the second light guide.
Figure 15C:
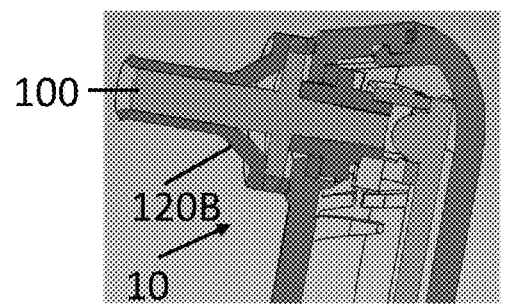

A second light guide 100B is shown in FIGS. 15A-C. The probe 106B of this light guide defines cylindrical post extending downwardly from the base 104. Although shown with a flat bottom surface, the probe could have a rounded or curved bottom surface. The distal end could also be faceted. The nose 1308 of the cover 1208 extends the full length of the probe 106B. As such, light only exits through the end of the probe 106B. The probe 106B is designed for external use to transilluminate the tooth crown and to cure pre-endodontic and post endodontic restoration materials. In addition, the probe 106B can be used to illuminate select tissue areas (i.e., of the gum or check), and thus, when used with a light of the proper wavelength, can be used to detect certain cancers, such as oral cancer.

Figure 16A:
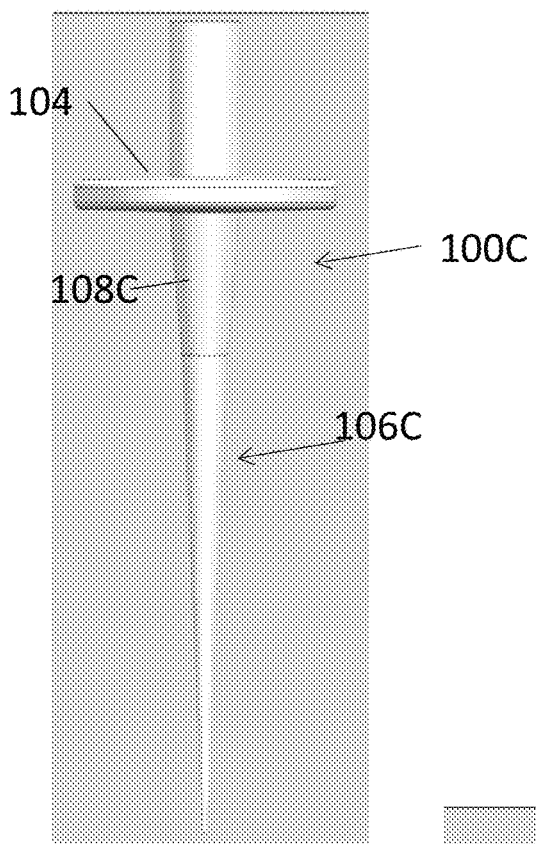
FIGS. 16A-B are elevational and bottom perspective views, respectively of a third light guide.
Figure 16B:
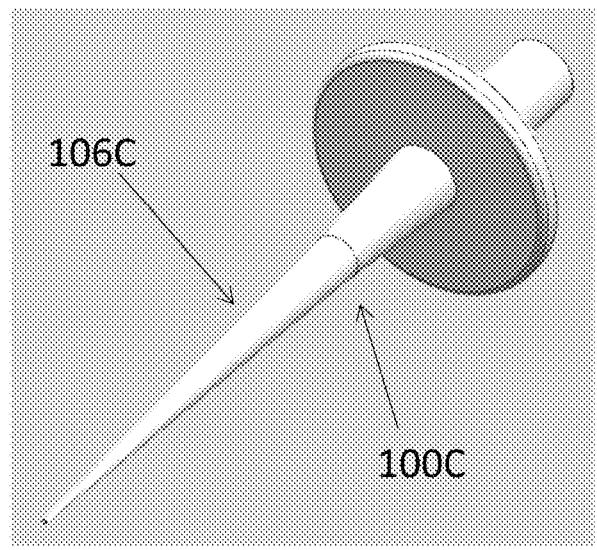
Figure 16C:
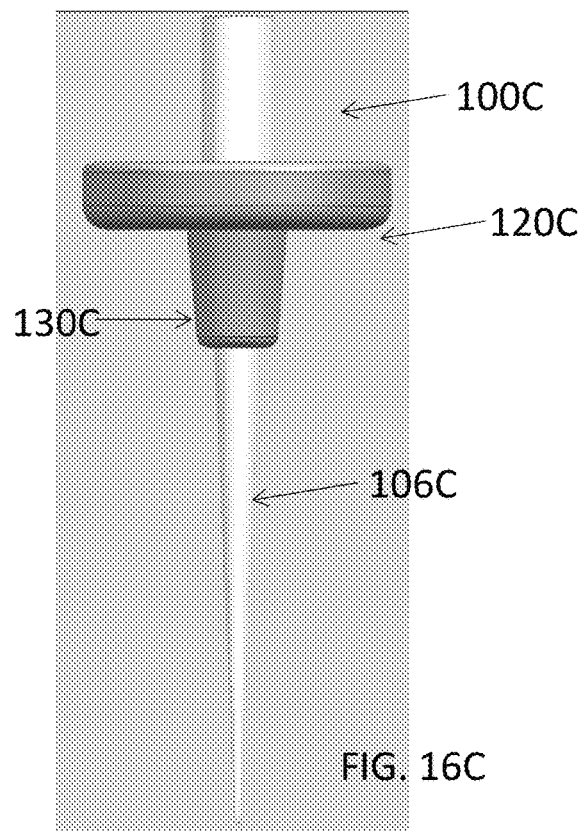
FIG. 16C is an elevational view of the third light guide with an associated shield.

A third light guide 100C is shown in FIGS. 16A-C. The probe 106C of the light guide 100C is an elongate tapering probe sized and shaped to extend to the apical end of a root canal. The probe can, for example, be 20 mm long. The probe 106C includes an upper tapered connection section 108C which connects the probe 106C to the base plate 104. The nose 130C of the cover 120C is sized and shaped to encase the connecting portion 108C. The light guide 100C can be used to transilluminate a tooth root from within the root canal to facilitate detection of cracks and other abnormalities in the tooth root. As such, the light guide 100C is primarily intended to be a static guide. However, it could be driven in the canal by the motor to activate fluid within the canal.

Figure 17A:
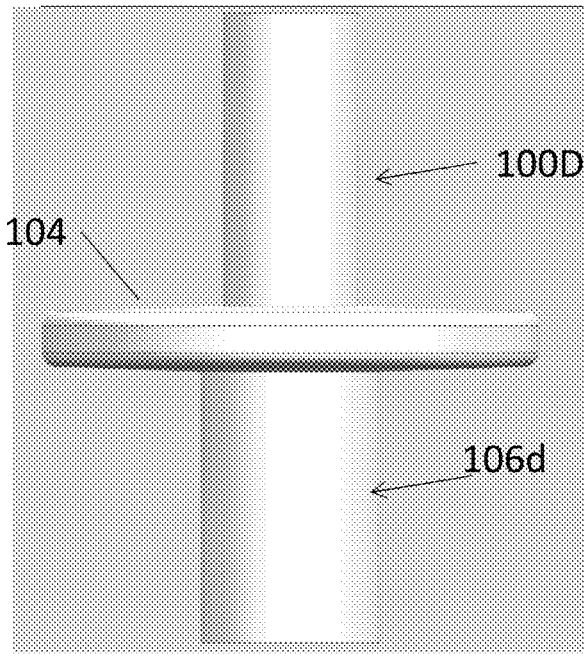
FIGS. 17A-B are elevational and bottom perspective views, respectively of a fourth light guide.
Figure 17B:
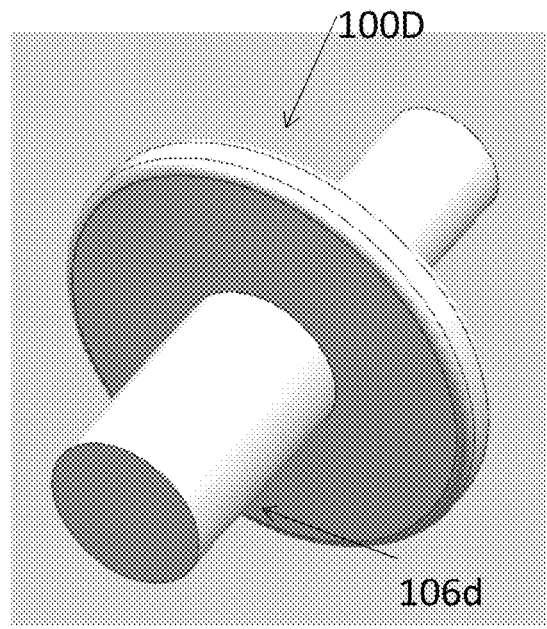
Figure 17C:
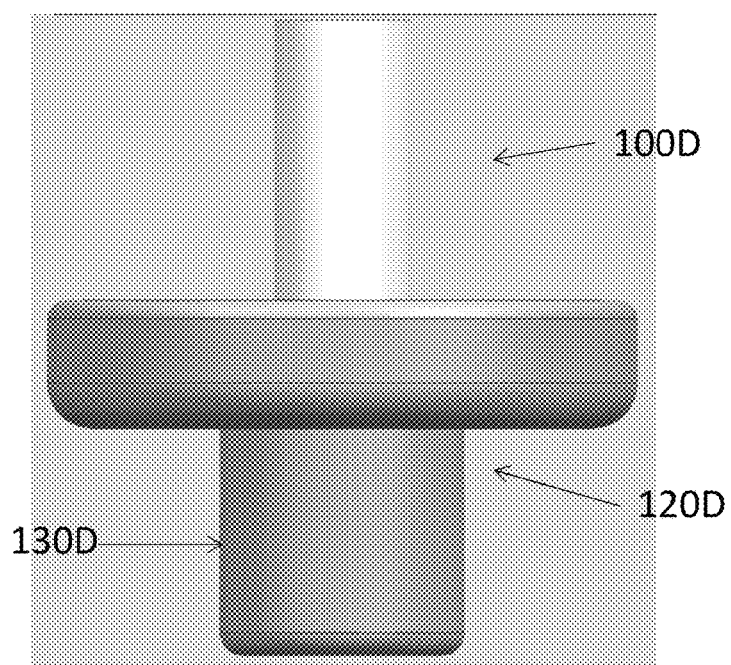
FIG. 17C is an elevational view of the fourth light guide with an associated shield.

A fourth light guide 100D is shown in FIGS. 17A-C. The probe 106D of the light guide 100D is generally cylindrical with a flat bottom surface. However, it is shorter and wider than the light probe 1008. The light probe 106D can have a length of 5 mm and a width of 4 mm (for a L:W ratio of 5:4). The nose 130D of the cover 120D extends the full length of the probe 106D, and thus, the light will exit primarily through the end of the probe. To further reduce the potential for light exiting the light guide other than at the end of the probe 106D, the sides of the probe and the surfaces of the base plate 104 can be coated with a light-opaque material, such as a silicon or a metallic coating. The light guide 100D is intended for use as an illumination light guide to provide illumination with a mouth or treatment area, transilluminate the crown externally, and to cure materials, such as restoration materials and cavity filling materials. The width of the probe 106D will allow the probe to be inserted into access cavities in crowns of certain teeth (for example, molars), and could be used to transilluminate a crown from within the access cavity.

Figure 18A:
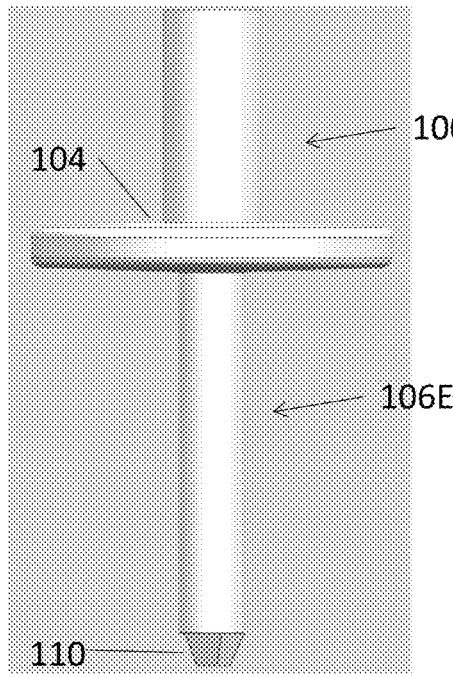
FIGS. 18A-C are elevational, bottom perspective, and bottom plan views, respectively of a fifth light guide.
Figure 18B:
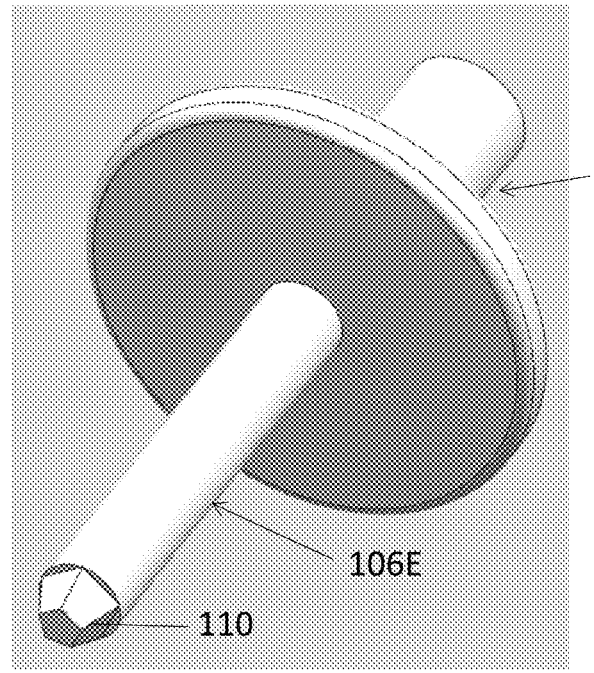
Figure 18C:
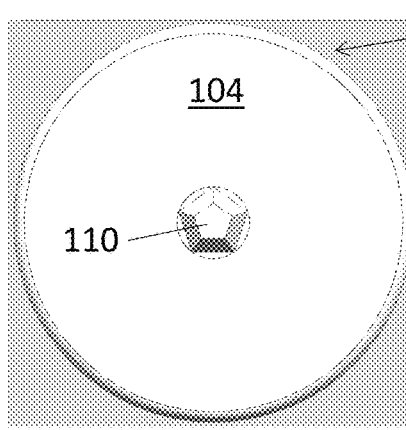
Figure 18D:
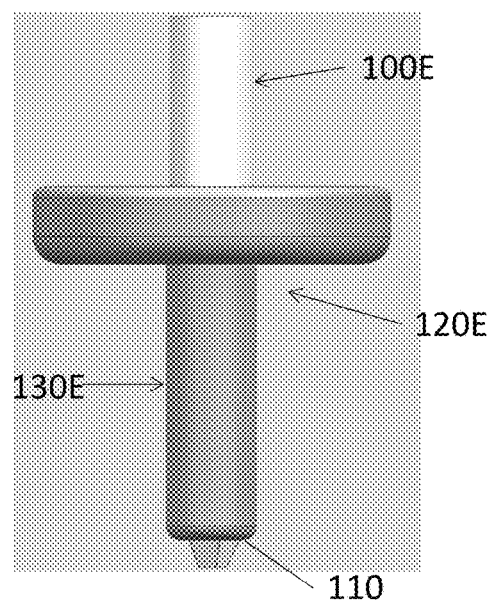
FIG. 18D is an elevational view of the fifth light guide with an associated shield.
Figure 18E:
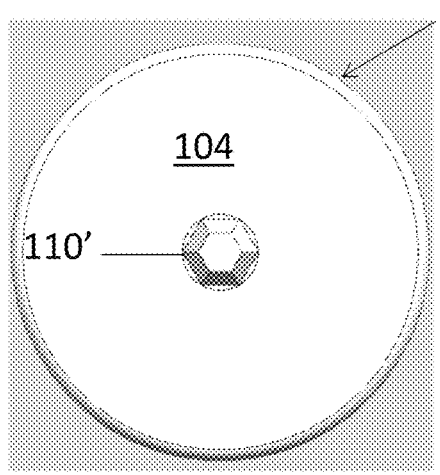
FIGS. 18E-F are bottom plan views showing variations of the distal end of the fifth light guide
Figure 18F:
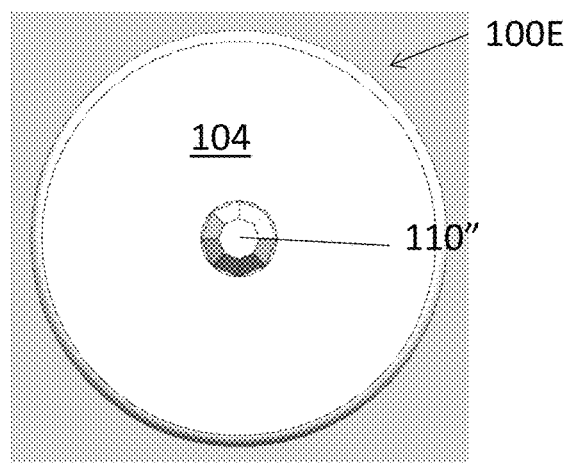

A fifth light guide 100E is shown in FIGS. 18A-C. The probe 106E of the light guides 100E is cylindrical, with a long narrow profile. For example, the light probe 106E can have a length of 10 mm and a width of 2 mm (for a L:W ratio of 5:1). The probe 100E, however, differs in that it has an end portion 110E in the form of a prism at the distal end of the probe. The prism 110E is illustratively shown to have a flat bottom surface in the shape of a pentagon, with walls sloping upwardly and outwardly form each edge of the base. The nose 130E of the cover 120E extends the length of the probe, such that just the prism 110E extends from the end of the nose 130E. Light thus exits the light through the facets (bottom and sides) of the prism 110E. The diameter of the probe allows for the probe to extend at least partially into a prepared root canal. The probe 106E can thus be used to transilluminate the tooth root and the tooth crown and to cure materials in the root and crown. As such, the light guide 100E is primarily a static light guide. FIGS. 18E-F show two variations of the light guide 100E. The light guides of FIGS. 18E-F are identical to the light guide of FIGS. 18A-D, except for the prism at the distal end of the probe. If FIG. 18E, the prism is hexagonal and in FIG. 18F, the prism is octagonal. As seen in FIGS. 18D-F, bottom surfaces of the prisms all define regular polygons. By changing the number of side surfaces of the prisms, the direction the light is transmitted will be altered slightly.

Figure 19A:
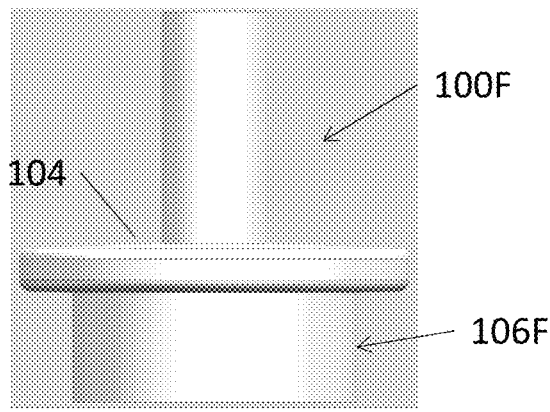
FIGS. 19A-B are elevational and bottom perspective views, respectively of a sixth light guide.
Figure 19B:
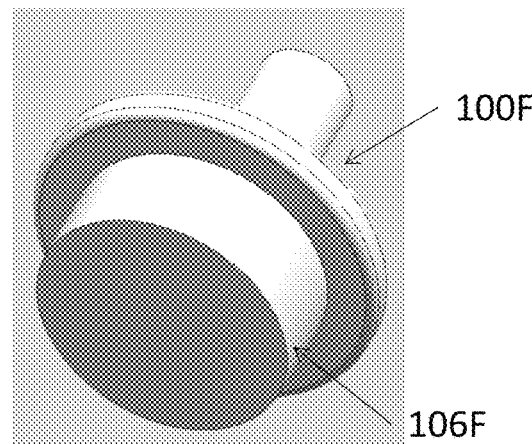
Figure 19C:
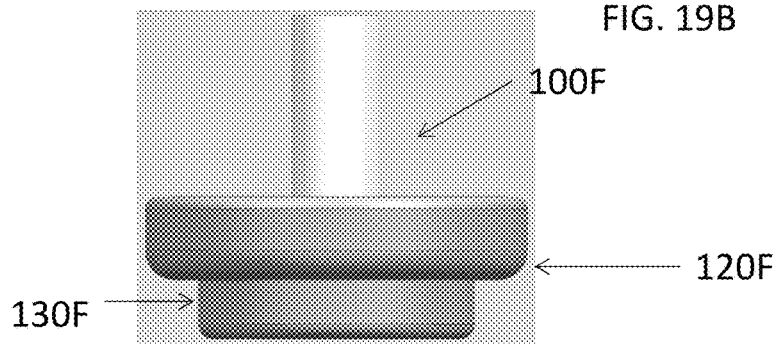
FIG. 19C is an elevational view of the sixth light guide with an associated shield.
Figure 21A:
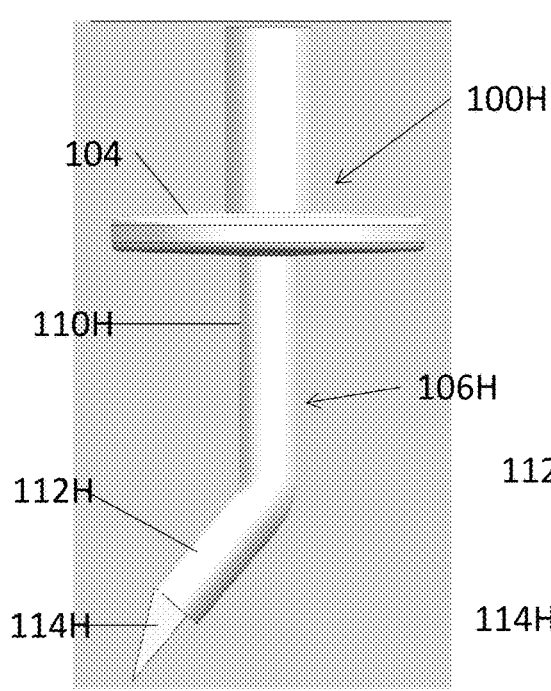
FIGS. 21A-C are elevational, bottom perspective, and front perspective views, respectively of a eighth light guide.
Figure 21B:
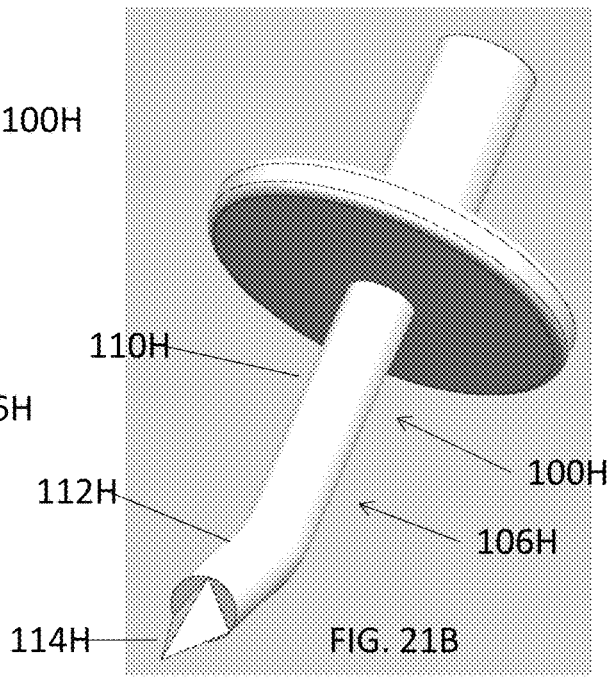
Figure 21C:
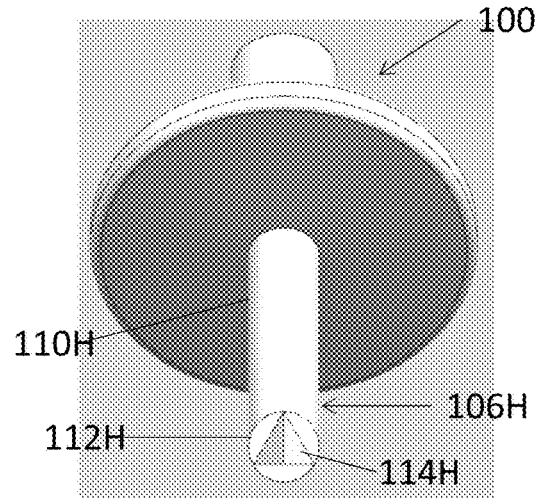
Figure 21D:
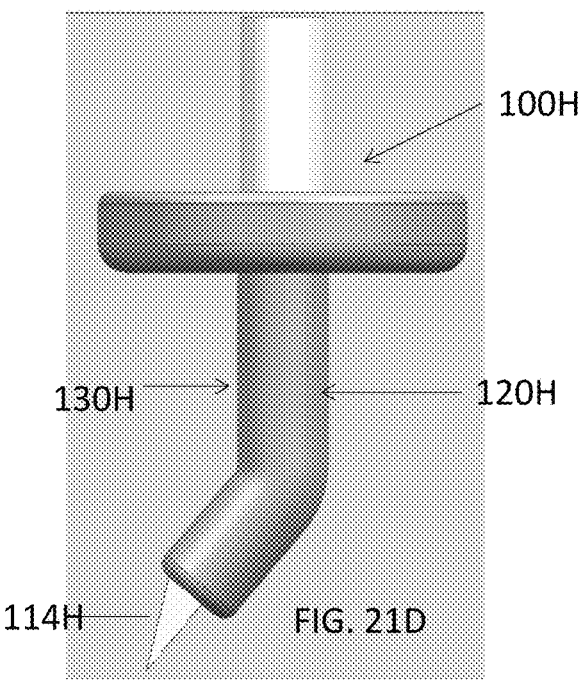
FIG. 21D is an elevational view of the eighth light guide with an associated shield.

A sixth light guide 100F is shown in FIGS. 19A-C. The probe 106F of the light guide 100F is cylindrical with a flat bottom surface. For example, the light probe 106F can have a length of 2 mm and a width of 8 mm (for a L:W ratio of 1:4). As such, the probe 106F is generally a squat or blunt probe. The nose 130F of the cover 120E surrounds full side wall of the probe 106F such that light exits primarily through the bottom of the probe. The large diameter of the probe renders the probe too large to fit into the access cavity of a tooth. However, the material from which the cover 120F is made is malleable or conformable. Thus, when the probe is be pressed against the upper surface of a tooth or access cavity, the cover will conform to the shape of the tooth rim to form a seal with the tooth rim. This will allow for the probe to be used to transilluminate the access cavity or crown of the tooth from within, to facilitate detection of cracks within the tooth. In addition, the light guide can be used to illuminate soft tissue (i.e., check or gum tissue) to detect abnormalities in the soft tissue, including certain oral cancers.

A seventh light guide 100G is shown in FIGS. 20A-C. The probe 106G of the light guide 100G defines a generally elongate cylinder. The bottom surface of the probe 106G is shown to be flat, but could be rounded or faceted. The probe 106G is sized to fit into a canal to reach the apical end of the canal. The probe thus has a diameter of 2 mm or less and a length of 15-20 mm. The nose 130G of the cover 120 extends the full length of the probe 106G, such that light primarily exits the bottom of the light probe 106G. Because the light exits the probe only at the bottom of the probe, the probe 106G can be used to direct light into a root canal to illuminate only portions of the canal below the distal end of the probe. This will allow the practitioner to study individual areas of the root canal to, for example, better determine where a crack begins and ends. Additionally, the probe 106G can be used to cure materials within the canal or in the access cavity.

An eighth light guide 100H is shown in FIGS. 21A-D. The light probe 106H of the light guide 100H is generally cylindrical and comprises an upper portion 110H which depends generally perpendicularly from (normal to) the base 104. A lower portion 112H angles extends from the distal end of the upper portion at an angle of about 30°-60°, and preferably about 40°-50°. Finally, an end portion 114H extends from the distal end of the probe's lower portion 12H. The end portion 114H is shown to be a tapering triangle. That is, it has a triangular base at the distal end of the probe 106H, and the three sides of the triangle taper to a point. The nose 130H of the cover 120H extends the length of the probe, such that only the end portion 114H extends from the end of the nose 130H. The end portion 114H tapers to a size that permits the end portion to be used interproximally (i.e. to fit between adjacent teeth) and to extend slightly into the periodontal pocket. This probe 106H can thus be used to transilluminate to tooth crown to detect cracks in the crown and to transilluminate the gum surrounding the tooth to visualize bone in the gum. This facilitates monitoring bone loss in patients with periodontal disease. Although the end portion 114H is shown as a triangle, the end portion 114H could be a flexible narrow cylinder which can fit between the teeth.

A ninth light guide 100I is shown in FIGS. 22A-C. The probe 106I of the light guide 100I is an elongate tapering probe sized and shaped to extend into a gingival pocket. The distal end of the probe is thus preferably rounded to provide smooth surface to reduce the potential for scratching the gingival tissue in the pocket. The probe 106I includes an upper tapered connection section 108I which connects the probe 106I to the base plate 104. The nose 130I of the cover 120I is sized and shaped to encase the connecting portion 108I. The light guide 100I can be used to transilluminate a gingival pocket from within the pocket. This allows for the practitioner to visualize bone level and tooth attachment apparatus and to detect cracks in the tooth. As such, the light guide 100C is primarily intended to be a static guide. Additionally, the probe includes markings 112I spaced at even intervals, for example 5 mm. The probe 100I can thus be used to measure the depth of a periodontal pocket. In FIG. 22C, the probe 106I has a single marking 112I spaced midway between the distal end of the probe and the bottom of the nose 130I of the cover. FIGS. 22D-E show longer versions of the probe. The probe 106I' includes two marks 112I; and the probe 106I" includes three marks 112I. Thus, for example, the probes 106I, 106I' and 106I" can have varying lengths (e.g. of 10 mm, 15 mm, 20 mm).

In addition to transillumination, some of the light guides (such as light guides 100C (FIG. 16A-C), 100E (FIGS. 18E-F), 100G (FIGS. 20A-C)), can be used to locate the canal orifice at the base of the pulp chamber. For example, in a sclerosed (calcified) or obliterated root canal, the practitioner can apply a fluorescent dye (such as rose bengal) in the pulp chamber, gently rinse the pulp chamber, and then illuminate the floor of the pulp chamber using an appropriate light guide with an appropriate light wavelength (such as green light). The fluorescent dye in the orifice will light up—guiding the clinician to the root canal that leads from the orifice.

As can be seen, a variety of light probes are disclosed. The light probes can be grouped as active light probes (i.e., those which are intended to be rotatably or reciprocatingly driven, and static light probes (i.e., those which are intended to be used only transmit light, and thus are used without engaging the motor). Further, the side wall of the probes can be fully covered by the nose of the cover, so that light exits only the end of the probe, or the probes can extend from the nose, so that light can be transmitted from the sides of the probes. The probes can be provided with end portions (prisms) which allow for the light to be directed outwardly, rather than axially. Additionally, portions of any of the light guides can be coated with a light opaque material to direct light to exit the probe only through specific areas of the probe. For example, the side wall of the probe and the base plate 104 can be coated. If the coating is reflective, the coating will facilitate directing the light to desired exit points on the probe. The coating can block virtually 100% of the light, so that light cannot pass through the coating, such that light exits the light guide only in coating free areas. Alternatively, the coating can be one which allows for a desired fraction of the light to pass through. Thus, an upper portion of the probe can be provided with a coating that blocks, for example, 50% of the light, and a bottom portion of the probe can be uncoated. This would provide a probe in which light of a lesser intensity exits the upper portion of the probe than the lower portion of the probe. Further, different coatings which block different amounts of light can be used on a single probe, to provide a variation in light intensity along the length of the probe. Coatings can be applied via injection molding on (or even co-molding with) the probe, or can be applied via 3D printing, sputtering, vapor deposition, electrostatic deposition, or any other desired method.

As various changes could be made in the above constructions without departing from the scope of the invention, it is intended that all matter contained in the above description or shown in the accompanying drawings shall be interpreted as illustrative and not in a limiting sense. For example, although the handpiece battery is described to recharge wirelessly, the handpiece could have external electrical contacts on its bottom surface 13e which engage corresponding electrical contacts in the floor 33b of the charging base, such that the handpiece has a wired, rather than wireless, connection to the recharging base. Further, the handpiece could be wired, rather than cordless. In this instance, the battery could be omitted, and replaced with a power cord which would connect the handpiece to a source of electricity. Although the light guide is described to be frictionally received in the light guide holder/gear member 282, the light guide can be secured in the light guide holder by other means. For example, the light guide can be threaded into the light guide holder, the light guide and light guide holder can include a pin and a bayonet slot. Any other connection means can be used that will rotationally fix the light guide to the light guide holder. These examples are merely illustrative.

The invention claimed is:

1. A medical/dental handpiece, comprising:
a housing having a base portion, a central portion, distal portion, and a head at an end of said distal portion; said distal portion defining a first axis; said head having a first axial end and a second axial end arranged along a second axis; said first axis intersecting said second axis; said head further comprising a bottom surface at said second axial end defining an opening;
a motor having an output shaft; said motor being selectively switchable between an activated mode in which said output shaft rotates or reciprocates and a deactivated mode in which said output shaft neither rotates nor reciprocates;
an output shaft gear operatively driven by said motor;
a light source; said light source comprising one or more light producing elements selectively switchable between an activated mode in which said light source produces light, and a deactivated mode in which said light source does not produce light;
a light guide holder mounted in said head of said handpiece for rotation relative to said head; said light guide holder comprising a body having a first axial end and a second axial end, a gear portion shaped and configured to mesh with said output shaft gear, an axial passage extending from said second axial end toward said first axial end of said body of said light guide holder and being opened at least at said second axial end of said body of said light guide holder, whereby said light guide holder is adapted to removably receive a light guide in said axial passage whereby said light guide is rotationally fixed relative to the light guide holder when said light guide holder is being driven, said axial passage being axially aligned with said opening in said bottom surface of said head, whereby said light source is configured, such that when said light source is activated light from said light source will be directed axially into and through said passage of said light guide holder from said first end of said light guide holder;
said light guide holder and said output shaft gear being positioned in said housing such that said output shaft gear meshes with the teeth of said light guide holder, such that when said motor is activated, said light guide holder will be driven by said output shaft gear; and
an electric circuit for said handpiece; said electric circuit comprising said motor, said light source, and at least one switch; whereby said handpiece is operable in three modes: (1) only the motor is activated, (2) only the light source is activated, and (3) both the motor and light source are activated.

2. The medical/dental handpiece of claim 1, wherein said light source is configured to change the wavelength and/or intensity of the light produced by said light source.

3. The medical/dental handpiece of claim 2 wherein said light source comprises a plurality of discrete light producing elements; the electric circuit being configured to selectively activate only one of said discrete light producing elements or selectively activate two or more of said discrete light producing elements.

4. The medical/dental handpiece of claim 3 wherein said plurality of discrete light producing elements include at least two light producing elements which emit light in different wavelengths.

5. The medical/dental handpiece of claim 3 wherein said plurality of discrete light producing elements include at least two light producing elements which emit light at the same wavelength.

6. The medical/dental handpiece of claim 1, wherein said handpiece further comprises a driven output shaft operatively connected to said motor output shaft to be driven by said motor, said output shaft gear being proximate an end of said driven output shaft spaced from said motor; said output shaft gear being rotatable about first axis;
said light guide holder being rotatable about said second axis.

7. The medical/dental handpiece of claim 6, wherein said handpiece comprises a first bearing surface defining an arc in a plane generally perpendicular to the output shaft axis and a second bearing surface spaced from said bottom surface of said head; said output shaft gear defining a shoulder which rotates against said first bearing surface; and said second bearing surface being generally cylindrical and being sized to rotatably receive the first axial end of said body of said light guide holder.

8. The medical/dental handpiece of claim 7,
wherein the handpiece includes a gear cover received in said head of said handpiece;
said gear cover having first and second axial ends; said gear cover defining said first and second bearing surfaces; said gear cover being opened at its said second axial end to receive said light guide holder; said gear cover having an upper surface at said first axial end defining an opening aligned with said passage of said light guide holder; said light source being positioned to direct illumination through said opening of said gear cover.

9. The medical/dental device of claim 6 comprising a gear box assembly positioned between said motor and said driven output shaft; said gear box assembly comprising a plurality of intermeshing gears which reduce a torque and increase speed output by said motor to a desired torque and speed.

10. The medical/dental handpiece of claim 1, wherein said medical dental handpiece comprises first and second bearing surfaces in said head; said first and second bearing surfaces being sized and shaped to position said light guide holder and said output shaft gear in said head and to maintain said gear portion of said light guide holder in meshing engagement with said output shaft gear.

11. A medical/dental handpiece, comprising:
a housing having a base portion, a central portion, distal portion, and a head; said head having a bottom surface defining an opening;
a motor having an output shaft; said motor being selectively switchable between an activated mode in which said output shaft rotates or reciprocates and a deactivated mode in which said output shaft neither rotates nor reciprocates;
an output shaft gear operatively driven by said motor;
a light source; said light source comprising one or more light producing elements selectively switchable between an activated mode in which said light source produces light, and a deactivated mode in which said light source does not produce light;
a light guide holder mounted in said head of said handpiece for rotation relative to said head; said light guide holder comprising a sleeve and a circumferential flange on said sleeve; said circumferential flange having teeth on an upper surface thereof defining a light guide holder gear; said sleeve defining a passage therethrough which is axially aligned with said opening in said bottom surface of said head and said light source, whereby when activated light from said light source will be directed from above said passage in said sleeve into and through said passage of said light guide holder;
said light guide holder and said output shaft gear being positioned in said housing such that said output shaft gear meshes with the teeth of said light guide holder, such that when said motor is activated, said light guide holder will be driven by said output shaft gear;
an electric circuit for said handpiece; said electric circuit comprising said motor, said light source, and at least one switch; whereby said handpiece is operable in three modes: (1) only the motor is activated, (2) only the light source is activated, and (3) both the motor and light source are activated; and
a light guide, said light guide comprising a stem and a probe below said stem; said stem being sized to be removably received in said sleeve of said light guide holder such that said light guide will be driven by said light guide holder upon activation of said motor; said light guide being made at least in part of light transmitting material, whereby said light guide receives said illumination from said light source when said light source is activated, and said illumination passes through said light guide stem to exit through said probe of said light guide;
said light guide further comprising a plate between said stem and said probe; said plate being positioned adjacent an outer surface of said bottom surface of said head when said light guide is received in said light guide holder; said handpiece further comprising a cover comprising an attachment portion adapted to be connected to said plate of said light guide and a nose which extends from said attachment portion; said nose at least in part surrounding said probe.

12. The medical/dental handpiece of claim 11 wherein said cover is made from a flexible and conformable material such that when pressed against a surface; said cover will conform to the shape of said surface.

13. A medical/dental handpiece, comprising:
a housing having a base portion, a central portion, distal portion, and a head at an end of said distal portion; said head portion having a first axial end and a second axial end; said head including a bottom surface at said second axial end defining an opening;
a motor contained within said housing;
an output shaft operatively connected to said motor to be driven by said motor; said output shaft rotatable about an output shaft axis;
an output shaft gear rotationally fixed to said output shaft to be driven by the output shaft, wherein said output shaft gear comprises a distal gear portion,
a light guide holder rotatably mounted in said head; said light guide holder comprising a hollow sleeve defining a passage therethrough, a circumferential flange on said sleeve having teeth on one of an upper surface and a lower of said flange to define a light guide holder gear;

said sleeve having a first axial end an a second axial end and defining a passage extending from said second axial end to said first axial end of said sleeve; said passage being opened at least at said second axial end of said sleeve; said light guide holder gear being positioned in said head such that said passage of said sleeve is axially aligned with said opening in said bottom surface of said head; said light guide holder being rotatable about a light guide axis which is offset from said output shaft axis;

a first bearing surface and a second bearing surface in said head of said handpiece; said first bearing surface defining an arc in a plane generally perpendicular to the output shaft axis; said second bearing surface being spaced from the bottom surface of said handpiece head; said output shaft gear defining a shoulder which rotates against said first bearing surface; and said second bearing surface being generally cylindrical and being sized to rotatably receive said first axial end of said light guide holder sleeve; said first and second bearing surfaces positioning said output shaft gear and said light guide holder gear such that they mesh, wherein said light guide holder gear is rotationally driven rotationally by the output shaft gear; and a light source positioned in said handpiece, said handpiece being configured to direct light from said light source into the light guide holder sleeve from the first axial end of said sleeve when the light source is activated.

14. The medical/dental handpiece of claim 13, wherein said first and second bearing surfaces are defined by a gear cover received in said head; said gear cover having a first axial end and a second axial end; said gear cover being opened at its said second axial end to receive said light guide holder; said gear cover having an upper surface at its said first axial end defining an opening aligned with said sleeve of said light guide holder; said light from said light source being directed through said opening.

15. The medical/dental handpiece of claim 13, wherein said light guide holder is driven by the output shaft gear about an axis that is distinct from the axis of the output shaft gear.

16. The medical/dental handpiece of claim 13, wherein light guide holder is driven rotationally and/or reciprocatingly.

17. A medical/dental handpiece, comprising:
a housing having a base portion, a central portion, distal portion, and a head at an end of said distal portion; said head having a first axial end and a second axial end and comprising a bottom surface at said second axial end defining an opening;
a motor having an output shaft; said motor being selectively switchable between an activated mode in which said output shaft rotates or reciprocates and a deactivated mode in which said output shaft neither rotates nor reciprocates;
an output shaft gear operatively driven by said motor output shaft;
a light source; said light source comprising at least one or more light producing elements selectively switchable between an activated mode in which said light source produces light, and a deactivated mode in which said light source does not produce light;
a light guide holder mounted in said head of said handpiece for rotation relative to said head; said light guide holder comprising a body having a first axial end and a second axial end, an axial passage extending from said second axial end toward said first axial end of said body and being opened at least at said second axial end, said axial passage being axially aligned with said opening in said bottom surface of said head, whereby said light source is configured, such that when said light source is activated light from said light source will be directed axially into and through said passage of said light guide holder from said first axial end of said light guide holder; said light guide holder further including a gear portion shaped and configured to mesh with said output shaft gear such that said light guide holder is rotationally driven by said motor when said motor is activated, an electric circuit for said handpiece; said electric circuit comprising said motor, said light source, and at least one switch; whereby said handpiece is operable in three modes: (1) only the motor is activated, (2) only the light source is activated, and (3) both the motor and light source are activated; and a light guide, said light guide comprising a stem and a probe below said stem; said stem being sized to be removably received in said axial passage of said light guide holder such that said light guide is rotationally fixed relative to said light guide holder to be driven by said light guide holder upon activation of said motor; said light guide being made at least in part of a material through which light can pass, whereby said light guide receives said illumination from said light source when said light source is activated, and said illumination passes through said light guide stem to exit through said probe of said light guide.

18. The medical/dental handpiece of claim 17 wherein said light guide is solid.

19. The medical/dental handpiece of claim 17 wherein said light guide includes a coating at least on external walls of said probe, said coating being a coating which permits no light to pass through the coating or which permits an amount of the light to pass through the coating such that light exits the light probe only at desired portions or intensities of said light probe.

20. The medical/dental handpiece of claim 19 wherein said coating is one of a silicon coating or a reflective metal coating.

21. The medical/dental handpiece of claim 17 wherein said light guide further includes a base plate, said probe extending from a first side of said base plate and said stem extending from an opposite side of said base plate; the probe defining a taper along a length of said probe; said probe being sized to extend into a prepared root canal, an access cavity, clinical crown or a periodontal pocket adjacent a tooth.

22. The medical/dental handpiece of claim 21 wherein said probe includes at least one measurement marking along the length of the probe.

23. The medical/dental handpiece of claim 21 wherein said probe is shaped to mechanically activate fluid in a root canal or cavity upon activation of said motor.

24. The medical/dental handpiece of claim 17 wherein said probe is generally cylindrical in cross-section.

25. The medical/dental handpiece of claim 24 wherein said probe includes an end portion on a distal end of said probe.

26. The medical/dental handpiece of claim 25 wherein said end portion comprises a prism having an end surface in the form of a polygon and side surfaces extending from edges of said end surface to said distal end of said probe.

27. The medical/dental handpiece of claim 24 wherein said end portion is sized and shaped to be received in spaces between teeth or in periodontal pockets.

28. The medical/dental handpiece of claim 27 wherein said end portion comprises a triangular prism extending from said distal end of said probe.

29. The medical/dental handpiece of claim 24 wherein said probe defines an upper section and a lower section, said lower section angling away from said upper section.

30. The medical/dental handpiece of claim 24 further comprising a cover having a nose, wherein said nose of said cover extends substantially the full length of said probe, such that substantially only said end portion extends beyond the nose, such that light exits substantially only through said end portion.

31. The medical/dental handpiece of claim 24 wherein said probe has a diameter sized to enable said probe to extend into a tooth root canal.

32. The medical/dental handpiece of claim 24 wherein said probe has a diameter sized such that it will engage and cover an upper surface of a tooth when the probe is positioned on a tooth.

\* \* \* \* \*